US006255078B1

(12) United States Patent
Petrovskis et al.

(10) Patent No.: US 6,255,078 B1
(45) Date of Patent: Jul. 3, 2001

(54) PSEUDORABIES VIRUS PROTEIN CROSS REFERENCE TO RELATED APPLICATIONS

(75) Inventors: Erik Aivars Petrovskis; Leonard Edwin Post, both of Kalamazoo, MI (US); James G. Timmins, Naperville, IL (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 08/485,289

(22) Filed: Jun. 7, 1995

Related U.S. Application Data

(62) Division of application No. 08/262,813, filed on Jun. 21, 1994, now Pat. No. 5,674,709, which is a division of application No. 07/513,282, filed on Apr. 20, 1990, now Pat. No. 5,352,575, which is a continuation-in-part of application No. 07/100,817, filed on Jun. 29, 1987, now abandoned, which is a continuation of application No. PCT/US86/01761, filed on Aug. 28, 1986, which is a continuation-in-part of application No. 06/886,260, filed on Jul. 16, 1986, now abandoned, which is a continuation-in-part of application No. 06/844,113, filed on Mar. 26, 1986, now abandoned.

(51) Int. Cl.[7] .................................. C12N 5/38; C12N 5/10
(52) U.S. Cl. ................. 435/69.3; 435/252.3; 435/252.33; 435/254.11; 435/254.2; 435/325; 435/358; 435/362; 435/419; 536/23.72

(58) Field of Search ........................ 435/5, 810, 235.1, 435/236, 69.3, 252.3, 252.33, 254.11, 254.2, 325, 358, 362, 419; 424/89; 536/23.72

(56) References Cited

U.S. PATENT DOCUMENTS 4,711,850   12/1987   Kit et al. .................................. 435/235

OTHER PUBLICATIONS

Burgess et al. J. Cell Biology 111:2129–38, Nov. 1990.*
Lazar et al. Mol. Cell Biology 8(3):1247–52, Mar. 1988.*
Mettenleiter, T. et al., "Psudorabies Virus Avirulent Strains Fail to Express a Major Glycoprotein" *J. Virology* 56, 307–311 (1985). See entire document.

* cited by examiner

*Primary Examiner*—Laurie Scheiner
(74) *Attorney, Agent, or Firm*—Li-Hsien Rin-Laures M.D.; James D. Darnley, Jr.; Paul J. Koivuniemi

(57) ABSTRACT

The present invention provides recombinant DNA molecules comprising a sequence encoding a pseudorabies virus (PRV) glycoprotein selected from the group consisting of gI, gp50, and gp63, host cells transformed by said recombinant DNA molecule sequences, the gI, gp50 and gp63 polypeptides. The present invention also provides subunit vaccines for PRV, methods for protecting animals against PRV infection and methods for distinguishing between infected and vaccinated animals.

24 Claims, No Drawings

PSEUDORABIES VIRUS PROTEIN CROSS REFERENCE TO RELATED APPLICATIONS

CROSS REFERENCE TO RELATED APPLICATIONS

This application is a divisional application of U.S. Ser. No. 08/262,813, filed Jun. 21, 1994 now U.S. Pat. No. 5,674,709 which is a divisional of U.S. Ser. No. 07/513,282, filed Apr. 20, 1990 now U.S. Pat. No. 5,352,575; which was a continuation-in-part of U.S. Ser. No. 07/100,817 filed Jun. 29, 1987, abandoned; which was a continuation of International Patent Application No. PCT/US86/01761, filed Aug. 28, 1986; which was a continuation-in-part of U.S. Ser. No. 06/886,260, filed Jul. 16, 1986, abandoned; which was a continuation-in-part of U.S. Ser. No. 06/844,113, filed Mar. 26, 1986 now abandoned.

FIELD OF INVENTION

This invention relates to DNA sequences encoding pseudorabies virus glycoproteins and polypeptides related thereto. These DNA sequences are useful for screening animals to determine whether they are infected with PRV and also for expressing the glycoproteins encoded thereby.

BACKGROUND OF THE INVENTION

Pseudorabies virus (PRV) is a disease which infects many species of animals worldwide. PRV infections are variously called infectious Bulbar paralysis, Aujeszky's disease, and mad itch. Infections are known in important domestic animals such as swine, cattle, dogs, cats, sheep, rats and mink. The host range is very broad and includes most mammals and, experimentally at least, many kinds of birds (for a detailed list of hosts, see D. P. Gustafson, "Pseudorabies", in Diseases of Swine, 5th ed., A. D. Leman et al., eds., (1981)). For most infected animals the disease is fatal. Adult swine and possibly rats, however, are not killed by the disease and are therefore carriers.

Populations of swine are particularly susceptible to PRV. Although the adult swine rarely show symptoms or die from the disease, piglets become acutely ill when infected and death usually ensues in 24 to 48 hours often without specific clinical signs (T. C. Jones and R. D. Hunt, Veterinary Pathology, 5th ed., Lea & Febiger (1983)).

PRV vaccines have been produced by a variety of techniques and vaccination in endemic areas of Europe has been practiced for more than 15 years. Losses have been reduced by vaccination, but vaccination has maintained the virus in the environment. No vaccine has been produced that will prevent infection. Vaccinated animals that are exposed to virulent virus survive the infection and then shed more virulent virus. Vaccinated animals may therefore harbor a latent infection that can flare up again. (See, D. P. Gustafson, supra).

Live attenuated and inactivated vaccines for PRV are available commercially in the United States and have been approved by the USDA (See, C. E. Aronson, ed., Veterinary Pharmaceuticals & Biologicals, (1983)).

Because adult swine are carriers of PRV, many states have instituted screening programs to detect infected animals. DNA/DNA hybridization can be used to diagnose actively infected animals utilizing the DNA sequence of the instant invention. Some of the PRV glycoproteins of the present invention are also useful in producing diagnostics for PRV infections and also to produce vaccines against PRV.

PRV is a herpesvirus. The herpesviruses generally are among the most complex of animal viruses. Their genomes encode at least 50 virus specific proteins and contain upwards of 150,000 nucleotides. Among the most immunologically reactive proteins of herpesviruses are the glycoproteins found, among other places, in virion membranes and the membranes of infected cells. The literature on PRV glycoproteins refers to at least four viral glycoproteins (T. Ben-Porat and A. S. Kaplan, Virology, 41, pp. 265–73 (1970); A. S. Kaplan and T. Ben-Porat, Proc. Natl. Acad. Sci. USA, 66, pp. 799–806 (1970)).

INFORMATION DISCLOSURE

M. W. Wathen and L. K. Wathen, J. Virol., 51, pp. 57–62 (1984) refer to a PRV containing a mutation in a viral glycoprotein (gp50) and a method for selecting the mutant utilizing neutralizing monoclonal antibody directed against gp50. Wathen and Wathen also indicate that a monoclonal antibody directed against gp50 is a strong neutralizer of PRV, with or without the aid of complement, and that polyvalent immune serum is highly reactive against gp50, therefore concluding that gp50 may be one of the important PRV immunogens. On the other hand, it has been reported that monoclonal antibodies that react with the 98,000 MW envelope glycoprotein neutralize PRV infectivity but that monoclonal antibodies directed against some of the other membrane glycoproteins have very little neutralizing activity (H. Hampl, et al., J. Virol., 52, pp. 583–90 (1984); and T. Ben-Porat and A. S. Kaplan, "Molecular Biology of Pseudorabies Virus", in B. Roizman ed., The Herpesviruses, 3, pp. 105–73 (1984)).

L. M. K. Wathen, et al., Virus Research, 4, pp. 19–29 (1985) refer to the production and characterization of monoclonal antibodies directed against PRV glycoproteins identified as gp50 and gp83 and their use for passively immunizing mice against PRV infection.

A. K. Robbins, et al., "Localization of a Pseudorabies Virus Glycoprotein Gene Using an E. coli Expression Plasmid Library", in Herpesvirus, pp. 551–61 (1984), refer to the construction of a library of E. coli plasmids containing PRV DNA. They also refer to the identification of a PRV gene that encodes glycoproteins of 74,000 and 92,000 MW. They do not refer to the glycoproteins of the instant invention.

A. K. Robbins, et al., European patent application No. 85400704.4 (publication No. 0 162 738) refers to the isolation, cloning and expression of PRV glycoproteins identified as gII and gIII. They do not refer to the PRV glycoproteins of the instant invention.

T. C. Mettenleiter, et al., "Mapping of the Structural Gene of Pseudorabies Virus Glycoprotein A and Identification of Two Non-Glycosylated Precursor Polypeptides", J. Virol., 53, pp. 52–57 (1985), refer to the mapping of the coding region of glycoprotein gA (which they equate with gI) to the BamHI 7 fragment of PRV DNA. They also state that the BamHI 7 fragment codes for at least three other viral proteins of 65K, 60K, and 40K MW. They do not disclose or suggest the DNA sequence encoding the glycoproteins of the instant invention or the production of such polypeptides by recombinant DNA methods.

B. Lomniczi, et al., "Deletions in the Genomes of Pseudorabies Virus Vaccine Strains and Existence of Four Isomers of the Genomes", J. Virol., 49, pp. 970–79 (1984), refer to PRV vaccine strains that have deletions in the unique short sequence between 0.855 and 0.882 map units. This is in the vicinity of the gI gene. T. C. Mettenleiter, et al., "Pseudorabies Virus Avirulent Strains Fail to Express a Major Glycoprotein", J. Virol., 56, pp. 307–11 (1985), demonstrated that three commercial PRV vaccine strains lack glycoprotein gI. We have also found recently that the Bartha vaccine strain contains a deletion for most of the gp63 gene.

T. J. Rea et al., J. Virol., 54, pp. 21–29 (1985), refers to the mapping and the sequencing of the gene for the PRV glycoprotein that accumulates in the medium of infected cells (gX). Included among the flanking sequences of the gX gene shown therein is a small portion of the gp50 sequence, specifically beginning at base 1682 of FIG. 6 therein. However, this sequence was not identified as the gp50 sequence. Furthermore, there are errors in the sequence published by Rea et al. Bases 1586 and 1603 should be deleted. Bases should be inserted between bases 1708 and 1709, bases 1737 and 1738, bases 1743 and 1744 and bases 1753 and 1754. The consequence of these errors in the published partial sequence for gp50 is a frameshift. Translation of the open reading frame beginning at the AUG start site would give an incorrect amino acid sequence for the gp50 glycoprotein.

European published patent application 0 133 200 refers to a diagnostic antigenic factor to be used together with certain lectin-bound PRV glycoprotein subunit vaccines to distinguish carriers and noncarriers of PRV.

SUMMARY OF INVENTION

The present invention provides recombinant DNA molecules comprising DNA sequences encoding polypeptides displaying PRV glycoprotein antigenicity.

More particularly, the present invention provides host cells transformed with recombinant DNA molecules comprising the DNA sequences set forth in Charts A, B, and C, and fragments thereof.

The present invention also provides polypeptides expressed by hosts transformed with recombinant DNA molecules comprising DNA sequences of the formulas set forth in Charts A, B, and C, and immunologically functional equivalents and immunogenic fragments and derivatives of the polypeptides.

More particularly, the present invention provides polypeptides having the formulas set forth in Charts A, B, and C, immunogenic fragments thereof and immunologically functional equivalents thereof.

The present invention also provides recombinant DNA molecules comprising the DNA sequences encoding pseudorabies virus glycoproteins gp50, gp63, gI or immunogenic fragments thereof operatively linked to an expression control sequence.

The present invention also provides vaccines comprising gp50 and gp63 and methods of protecting animals from PRV infection by vaccinating them with these polypeptides.

DETAILED DESCRIPTION OF INVENTION

The existence and location of the gene encoding glycoprotein gp50 of PRV was demonstrated by M. W. Wathen and L. M. Wathen, supra.

The glycoprotein encoded by the gene was defined as a glycoprotein that reacted with a particular monoclonal antibody. This glycoprotein did not correspond to any of the previously known PRV glycoproteins. Wathen and Wathen mapped a mutation resistant to the monoclonal antibody, which, based on precedent in herpes simplex virus (e.g., T. C. Holland et al., J. Virol., 52, pp.566–74 (1984)), maps the location of the structural gene for gp50. Wathen and Wathen mapped the gp50 gene to the smaller SalI/BamHI fragment from within the BamHI 7 fragment of PRV. Rea et al, supra, have mapped the PRV glycoprotein gX gene to the same region.

The PRV gp63 and gI genes were isolated by screening PRV DNA libraries constructed in the bacteriophage expression vector λgt11 (J. G. Timmins, et al., "A method for Efficient Gene Isolation from Phage λgt Libraries: Use of Antisera to Denatured, Acetone-Precipitated Proteins", Gene, 39, pp. 89–93 (1985); R. A. Young and R. W. Davis, Proc. Natl. Acad. Sci. USA, 80, pp. 1194–98 (1983); R. A. Young and R. W. Davis, Science, 222, pp.778–82 (1983)).

PRV genomic DNA derived from PRV Rice strain originally obtained from D. P. Gustafson at Purdue University was isolated from the cytoplasm of PRV-infected Vero cells (ATCC CCL 81). The genomic DNA was fragmented by sonication and then cloned into λgt11 to produce a λ/PRV recombinant (λPRV) DNA library.

Antisera for screening the λPRV library were produced by inoculating mice with proteins isolated from cells infected with PRV (infected cell proteins or ICP's) that had been segregated according to size on SDS gels, and then isolating the antibodies. The λPRV phages to be screened were plated on a lawn of E. coli. λgt11 contains a unique cloning site in the 3' end of the lacZ gene. Foreign DNA's inserted in this unique site in the proper orientation and reading frame produce, on expression, polypeptides fused to β-galactosidase. A nitrocellulose filter containing an inducer of lacZ transcription to enhance expression of the PRV DNA was laid on top of the lawn. After the fusion polypeptides expressed by λPRV's had sufficient time to bind to the nitrocellulose filters, the filters were removed from the lawns and probed with the mouse antisera. Plaques producing antigen that bound the mice antisera were identified by probing with a labeled antibody for the mouse antisera.

Plaques that gave a positive signal were used to transform an E. coli host (Y1090, available from the ATCC, Rockville, Md. 20852). The cultures were then incubated overnight to produce the λPRV phage stocks. These phage stocks were used to infect E. coli K95 (D. Friedman, in The Bacteriophage Lambda, pp. 733–38, A. D. Hershey, ed. (1971)). Polypeptides produced by the transformed E. coli K95 were purified by preparative gel electrophoresis. Polypeptides that were overproduced (due to induction of transcription of the lacZ gene), having molecular weights greater than 116,000 daltons, and which were also absent from λgt11 control cultures were β-galactosidase-PRV fusion proteins. Each individual fusion protein was then injected into a different mouse to produce antisera.

Labeled PRV ICP's were produced by infecting Vero cells growing in a medium containing, for example, $^{14}$C-glucosamine (T. J. Rea, et al., supra.). The fusion protein antisera from above were used to immunoprecipitate these labeled ICP's. The polypeptides so precipitated were analyzed by gel electrophoresis. One of them was a 110 kd MW glycoprotein (gI) and another a 63 kd MW glycoprotein (gp63). The genes cloned in the phages that produced the hybrid proteins raising anti-gI and anti-gp63 serum were thus shown to be the gI and gp63 genes. These genes were found to map within the BamHI 7 fragment of the PRV genome (T. J. Rea, et al., supra.) as does the gp50 sequence (see Chart D). The gI location is in general agreement with the area where Mettenleiter, et al., supra, had mapped the gI gene. However, Mettenleiter, et al. implied that the gI gene extends into the BamHI 12 fragment which it does not.

This λPRV gene isolation method is rapid and efficient when compared to DNA hybridization and to in vitro translation of selected mRNAs. Because purified glycoproteins were unavailable, we could not construct, rapidly, oligonucleotide probes from amino acid sequence data, nor could we raise highly specific polyclonal antisera. Therefore we used the method set forth above.

As mentioned above, the genes encoding gp50, gp63, and gI mapped to the BamHI 7 fragment of the PRV DNA. The BamHI 7 fragment from PRV can be derived from plasmid pPRXh1 (also known as pUC1129) and fragments convenient for DNA sequence analysis can be derived by standard subcloning procedures. Plasmid pUC1129 is available from *E. coli* HB101, NRRL B-15772. This culture is available from the permanent collection of the Northern Regional Research Center Fermentation Laboratory (NRRL), U.S. Department of Agriculture, in Peoria, Ill., U.S.A.

*E. coli* HB101 containing pUC1129 can be grown up in L-broth by well known procedures. Typically the culture is grown to an optical density of 0.6 after which chloramphenicol is added and the culture is left to shake overnight. The culture is then lysed by, e.g., using high salt SDS and the supernatant is subjected to a cesium chloride/ethidium bromide equilibrium density gradient centrifugation to yield the plasmids.

The availability of these gene sequences permits direct manipulation of the genes and gene sequences which allows modifications of the regulation of expression and/or the structure of the protein encoded by the gene or a fragment thereof. Knowledge of these gene sequences also allows one to clone the corresponding gene, or fragment thereof, from any strain of PRV using the known sequence as a hybridization probe, and to express the entire protein or fragment thereof by recombinant techniques generally known in the art.

Knowledge of these gene sequences enabled us to deduce the amino acid sequence of the corresponding polypeptides (Charts A–C). As a result, fragments of these polypeptides having PRV immunogenicity can be produced by standard methods of protein synthesis or recombinant DNA techniques. As used herein, immunogenicity and antigenicity are used interchangeably to refer to the ability to stimulate any type of adaptive immune response, i.e., antigen and antigenicity are not limited in meaning to substances that stimulate the production of antibodies.

The primary structures (sequences) of the genes coding for gp50, gp63, and gI also are set forth in Charts A–C.

The genes or fragments thereof can be extracted from pUC1129 by digesting the plasmid DNA from a culture of NRRL B-15772 with appropriate endonuclease restriction enzymes. For example, the BamHI 7 fragment may be isolated by digestion of a preparation of pUC1129 with BamHI, and isolation by gel electrophoresis.

All restriction endonucleases referred to herein are commercially available and their use is well known in the art. Directions for use generally are provided by commercial suppliers of the restriction enzymes.

The excised gene or fragments thereof can be ligated to various cloning vehicles or vectors for use in transforming a host cell. The vectors preferably contains DNA sequences to initiate, control and terminate transcription and translation (which together comprise expression) of the PRV glycoprotein genes and are, therefore, operatively linked thereto. These "expression control sequences" are preferably compatible with the host cell to be transformed. When the host cell is a higher animal cell, e.g., a mammalian cell, the naturally occurring expression control sequences of the glycoprotein genes can be employed alone or together with heterologous expression control sequences. Heterologous sequences may also be employed alone. The vectors additionally preferably contain a marker gene (e.g., antibiotic resistance) to provide a phenotypic trait for selection of transformed host cells. Additionally a replicating vector will contain a replicon.

Typical vectors are plasmids, phages, and viruses that infect animal cells. In essence, one can use any DNA sequence that is capable of transforming a host cell.

The term host cell as used herein means a cell capable of being transformed with the DNA sequence coding for a polypeptide displaying PRV glycoprotein antigenicity. Preferably, the host cell is capable of expressing the PRV polypeptide or fragments thereof. The host cell can be procaryotic or eucaryotic. Illustrative procaryotic cells are bacteria such as *E. coli, B. subtilis,* Pseudomonas, and *B. stearothermophilus.* Illustrative eucaryotic cells are yeast or higher animal cells such as cells of insect, plant or mammalian origin. Mammalian cell systems often will be in the form of monolayers of cells although mammalian cell suspensions may also be used. Mammalian cell lines include, for example, VERO and HeLa cells, Chinese hamster ovary (CHO) cell lines, WI38, BHK, COS-7 or MDCK cell lines. Insect cell lines include the Sf9 line of *Spodoptera frugiperda* (ATCC CRL1711). A summary of some available eucaryotic plasmids, host cells and methods for employing them for cloning and expressing PRV glycoproteins can be found in K. Esser, et al., Plasmids of Eukaryotes (Fundamentals and Applications), Springer-Verlag (1986) which is incorporated herein by reference.

As indicated above, the vector, e.g., a plasmid, which is used to transform the host cell preferably contains compatible expression control sequences for expression of the PRV glycoprotein gene or fragments thereof. The expression control sequences are, therefore, operatively linked to the gene or fragment. When the host cells are bacteria, illustrative useful expression control sequences include the trp promoter and operator (Goeddel, et al., Nucl. Acids Res., 8, 4057 (1980)); the lac promoter and operator (Chang, et al., Nature, 275, 615 (1978)); the outer membrane protein promoter (EMBO J., 1, 771–775 (1982)); the bacteriophage λ promoters and operators (Nucl. Acids Res., 11, 4677–4688 (1983)); the α-amylase (*B. subtilis*) promoter and operator, termination sequences and other expression enhancement and control sequences compatible with the selected host cell. When the host cell is yeast, illustrative useful expression control sequences include, e.g., α-mating factor. For insect cells the polyhedrin promoter of baculoviruses can be used (Mol. Cell. Biol., 3, pp. 2156–65 (1983)). When the host cell is of insect or mammalian origin illustrative useful expression control sequences include, e.g., the SV-40 promoter (Science, 222, 524–527 (1983)) or, e.g., the metallothionein promoter (Nature, 296, 39–42 (1982)) or a heat shock promoter (Voellmy, et al., Proc. Natl. Acad. Sci. USA, 82, pp. 4949–53 (1985)). As noted above, when the host cell is mammalian one may use the expression control sequences for the PRV glycoprotein gene but preferably in combination with heterologous expression control sequences.

The plasmid or replicating or integrating DNA material containing the expression control sequences is cleaved using restriction enzymes, adjusted in size as necessary or desirable, and ligated with the PRV glycoprotein gene or fragments thereof by means well known in the art. When yeast or higher animal host cells are employed, polyadenylation or terminator sequences from known yeast or mammalian genes may be incorporated into the vector. For example, the bovine growth hormone polyadenylation sequence may be used as set forth in European publication number 0 093 619 and incorporated herein by reference. Additionally gene sequences to control replication of the host cell may be incorporated into the vector.

The host cells are competent or rendered competent for transformation by various means. When bacterial cells are the host cells they can be rendered competent by treatment with salts, typically a calcium salt, as generally described by Cohen, PNAS, 69, 2110 (1972). A yeast host cell generally is rendered competent by removal of its cell wall or by other means such as ionic treatment (J. Bacteriol., 153, 163–168 (1983)). There are several well-known methods of introducing DNA into animal cells including, e.g., calcium phosphate precipitation, fusion of the recipient cells with bacterial protoplasts containing the DNA, treatment of the recipient cells with liposomes containing the DNA, and microinjection of the DNA directly into the cells.

The transformed cells are grown up by means well known in the art (Molecular Cloning, Maniatis, T., et al., Cold Spring Harbor Laboratory, (1982); Biochemical Methods In Cell Culture And Virology, Kuchler, R. J., Dowden, Hutchinson and Ross, Inc., (1977); Methods In Yeast Genetics, Sherman, F., et al., Cold Spring Harbor Laboratory, (1982)) and the expressed PRV glycoprotein or fragment thereof is harvested from the cell medium in those systems where the protein is excreted from the host cell, or from the cell suspension after disruption of the host cell system by, e.g., mechanical or enzymatic means which are well known in the art.

As noted above, the amino acid sequences of the PRV glycoproteins as deduced from the gene structures are set forth in Charts AC. Polypeptides displaying PRV glycoprotein antigenicity include the sequences set forth in Chart A–C and any portions of the polypeptide sequences which are capable of eliciting an immune response in an animal, e.g., a mammal, which has been injected with the polypeptide sequence and also immunogenically functional analogs of the polypeptides.

As indicated hereinabove the entire gene coding for the PRV glycoprotein can be employed in constructing the vectors and transforming the host cells to express the PRV glycoprotein, or fragments of the gene coding for the PRV glycoprotein can be employed, whereby the resulting host cell will express polypeptides displaying PRV antigenicity. Any fragment of the PRV glycoprotein gene can be employed which results in the expression of a polypeptide which is an immunogenic fragment of the PRV glycoprotein or an analog thereof. As is well known in the art, the degeneracy of the genetic code permits easy substitution of base pairs to produce functionally equivalent genes and fragments thereof encoding polypeptides displaying PRV glycoprotein antigenicity. These functional equivalents also are included within the scope of the invention.

Charts D–S are set forth to illustrate the constructions of the Examples. Certain conventions are used to illustrate plasmids and DNA fragments as follows:

(1) The single line figures represent both circular and linear double-stranded DNA.

(2) Asterisks (*) indicate that the molecule represented is circular. Lack of an asterisk indicates the molecule is linear.

(3) Endonuclease restriction sites of interest are indicated above the line.

(4) Genes are indicated below the line.

(5) Distances between genes and restriction sites are not to scale. The figures show the relative positions only unless indicated otherwise.

Most of the recombinant DNA methods employed in practicing the present invention are standard procedures, well known to those skilled in the art, and described in detail, for example, in Molecular Cloning, T. Maniatis, et al., Cold Spring Harbor Laboratory, (1982) and B. Perbal, A Practical Guide to Molecular Cloning, John Wiley & Sons (1984), which are incorporated herein by reference.

EXAMPLE 1

In this example we set forth the sequencing, cloning and expression of PRV glycoprotein gp50.

1. Sequencing of the gp50 Gene

The BamHI 7 fragment of PRV Rice strain DNA (Chart D) which encodes the gp50 gene is isolated from pPRXh1 [NRRL B-15772], supra., and subcloned into the BamHI site of plasmid pBR322 (Maniatis et al., supra.).

Referring now to Chart E, the fragment is further subcloned using standard procedures by digesting BamHI 7 with PvuII, isolating the two BamHI/PvuII fragments (1.5 and 4.9 kb) and subcloning them between the BamHI and PvuII sites of pBR322 to produce plasmids pPR28-4 and pPR28-1 incorporating the 1.5 and 4.9 kb fragments respectively (see also, Rea et al., supra.). These subclones are used as sources of DNA for DNA sequencing experiments.

Chart F shows various restriction enzyme cleavage sites located in the gp50 gene and flanking regions. The 1.5 and 4.9 kb fragments subcloned above are digested with these restriction enzymes. Each of the ends generated by the restriction enzymes is labeled with $\gamma$-$^{32}$P-ATP using polynucleotide kinase and sequenced according to the method of Maxam and Gilbert, Methods Enzymol., 65, 499–560 (1980). The entire gene is sequenced at least twice on both strands. The DNA sequence for gp50 is set forth in Chart A. This DNA may be employed to detect animals actively infected with PRV. For example, one could take a nasal or throat swab, and then do a DNA/DNA hybridization by standard methods to detect the presence of PRV.

2. Expression of gp50

Referring now to Chart G, a NarI cleavage site is located 35 base pairs upstream from the gp50 gene initiation codon. The first step in expression is insertion of the convenient BamHI cleavage site at the point of the NarI cleavage site. Plasmid pPR28-4 from above is digested with restriction endonuclease NarI to produce DNA fragment 3 comprising the N-terminus encoding end of the gp50 gene and a portion of the gX gene. BamHI linkers are added to fragment 3 and the fragment is digested with BamHI to delete the gX sequence thus producing fragment 4. The BamHI ends are then ligated to produce plasmid pPR28-4 Nar2.

Referring now to Chart H, we show the assembly of the complete gp50 gene. pPR28-4 Nar2 is digested with BamHI and PvuII to produce fragment 5 (160 bp) comprising the N-terminal encoding portion of the gp50 gene. Plasmid pPR28-1 from above is also digested with PvuII and BamHI to produce a 4.9 kb fragment comprising the C-terminal encoding portion of the gp50 gene (fragment 6). Plasmid pPGX1 (constructed as set forth in U.S. patent application Ser. No. 760,130)), or, alternatively, plasmid pBR322, is digested with BamHI, treated with bacterial alkaline phosphatase (BAP) and then ligated with fragments 5 and 6 to produce plasmid pBGP50-23 comprising the complete gp50 gene.

Referring now to Chart I, we show the production of plasmid pD50. Plasmid pBG50-23 is cut with restriction enzyme MaeIII (K. Schmid et al., Nucl. Acids Res., 12, p. 2619 (1984)) to yield a mixture of fragments. The MaeIII ends are made blunt with T4 DNA polymerase and EcoRI linkers are added to the blunt ends followed by EcoRI digestion. The resulting fragments are cut with BamHI and a 1.3 kb BamHI/EcoRI fragment containing the gp50 gene (fragment 7) is isolated. Plasmid pSV2dhfr (obtained from the American Type Culture Collection, Bethesda Research Laboratories, or synthesized according to the method of S. Subramani, et al., Mol. Cell. Biol., 2, pp. 854–64 (1981)) is digested with BamHI and EcoRI and the larger (5.0 kb) fragment is isolated to produce fragment 8 containing the dihydrofolate reductase (dhfr) marker. Fragments 7 and 8 are then ligated to produce plasmid pD50 comprising the gp50 gene and the dhfr marker.

Referring now to Chart J, the immediate early promoter from human cytomegalovirus Towne strain is added upstream from the gp50 gene. pD50 is digested with BamHI and treated with bacterial alkaline phosphatase to produce fragment 9. A 760 bp Sau3A fragment containing the human cytomegalovirus (Towne) immediate early promoter is isolated according to the procedure set forth in U.S. patent application Ser. No. 758,517 to produce fragment 10 (see also, D. R. Thomsen, et al., Proc. Natl. Acad. Sci. USA, 81, pp. 659–63 (1984)). These fragments are then ligated by a BamHI/Sau3A fusion to produce plasmid pDIE50. To confirm that the promoter is in the proper orientation to transcribe the gp50 gene the plasmid is digested with SacI and PvuII and a 185 bp fragment is produced.

Referring now to Chart K, the 0.6 kb PvuII/EcoRI fragment containing the bovine growth hormone polyadenylation signal is isolated from plasmid pGH2R2 (R. P. Woychik, et al., Nucl. Acids Res., 10, pp. 7197–7210 (1982) by digestion with PvuII and EcoRI or from pSVCOW7 (supra.) to produce fragment 11.

Fragment 11 is cloned between the EcoRI and SmaI cleavage sites of pUC9 (obtained from Pharmacia/PL or ATCC) to give pCOWT1. pCOWT1 is cut with SalI, the ends made blunt with T4 DNA polymerase, EcoRI linkers are added, the DNA is cut with EcoRI, and the 0.6 kb fragment (fragment 12) is isolated. This is the same as fragment 11 except that it has two EcoRI ends and a polylinker sequence at one end.

Plasmid pDIE50 is cut with EcoRI, and fragment 12 is cloned into it to produce plasmid pDIE50PA. Digestion with BamHI and PvuII produces a fragment of 1.1 kb in the case where the polyadenylation signal is in the proper orientation. The plasmid can also be constructed by cloning in the polyadenylation sequence before the promoter.

Plasmid pDIE50PA is used to transfect CHO dhfr⁻ cells (DXB-11, G. Urlaub and L. A. Chasin, Proc. Natl. Acad. Sci. USA, 77, pp. 4216–20 (1980)) by calcium phosphate co-precipitation with salmon sperm carrier DNA (F. L. Graham and A. J. Van Der Eb, Virol., 52, pp. 456–67 (1973)). The dihydrofolate reductase positive (dhfr⁺) transfected cells are selected in Dulbecco's modified Eagle's medium plus Eagle's non-essential amino acids plus 10% fetal calf serum. Selected dhfr⁺ CHO cells produce gp50 as detected by immunofluorescence with anti-gp50 monoclonal antibody 3A-4, or by labelling with 14C-glucosamine and immunoprecipitation with 3A-4. Monoclonal antibody 3A-4 is produced as described in copending U.S. patent application Ser. No. 817,429, filed Jan. 9, 1985. Immunoprecipitation reactions are performed as described previously (T. J. Rea, et al., supra.) except for the following: The extracts are first incubated with normal mouse serum, followed by washed *Staphylococcus aureus* cells, and centrifuged for 30 minutes in a Beckman SW50.1 rotor at 40,000 rpm. After extracts are incubated with monoclonal or polyclonal antiserum plus *S. Aureus* cells, the cells are washed three times in 10 mM Tris HCl, pH 7.0, 1 mM EDTA, 0.1 M NaCl, 1% NP40 and 0.5% deoxycholate. Analysis of proteins is done on 11% SDS polyacrylamide gels (L. Morse, et al., J. Virol., 26, pp. 389–410 (1984)). In preliminary immunofluorescence assays it was found that 3A-4 reacted with the pDIE50PA-transfected CHO cells but not with untransfected CHO cells. When the transfected CHO cells were labelled with $^{14}$C-glucosamine, 3A-4 immunoprecipitated a labelled protein from cells containing pDIE50PA but not from control cells making human renin. The precipitated protein co-migrated on SDS-polyacrylamide gels with the protein precipitated by 3A-4 from PRV-infected cells.

A clone of these transfected CHO cells producing gp50 can be grown in roller bottles, harvested in phosphate buffered saline plus 1 mM EDTA, and mixed with complete Freund's adjuvant for use as a vaccine.

The gp50 gene can also be expressed in a vaccinia vector. In this embodiment, after pBG50-23 is digested with MaeIII and the ends made blunt with T4 DNA polymerase, the DNA is digested with BamHI. The 1.3 BamHI/blunt-ended fragment containing the gp50 gene is isolated. Plasmid pGS20 (Mackett, et al., J. Virol., 49, pp. 857–64 (1984)) is cut with BamHI and SmaI, and the larger 6.5 kb fragment is isolated by gel electrophoresis. These two fragments are ligated together to produce pVV50. Plasmid pVV50 is transfected into CV-1 cells (ATCC CCL 70) infected with the WR strain of vaccinia virus (ATCC VR-119), and selected for thymidine kinase negative recombinants by plating on 143 cells (ATCC CRL 8303) in 5-bromodeoxyuridine (BUdR) by the methods described by Mackett, et al. in DNA Cloning, Volume II: A Practical Approach, D. M. Clover, ed., IRL Press, Oxford (1985). The resulting virus, vaccinia-gp50, expressed gp50 in infected cells, as assayed by labelling of the proteins of the infected cell with $^{14}$C-glucosamine and immunoprecipitation with monoclonal antibody 3A-4.

EXAMPLE 2

In this example we set forth the protection of mice and swine from PRV challenge using the gp50 of Example 1 as an immunogenic agent.

In Tables 1–3, infra, the microneutralization assay was done as follows: Serial two-fold dilutions of serum samples were done in microtiter plates (Costar) using basal medium Eagle (BME) supplemented with 3% fetal calf serum and antibiotics. About 1000 pfu (50 μl) of PRV were added to 50 μl of each dilution. Rabbit complement was included in the virus aliquot at a dilution of 1:5 for the mouse serum assays but not the pig serum assays. The samples were incubated for either 1 hr (swine sera) or 3 hrs (mouse sera) at 37° C.

After the incubation period, an aliquot (50 μl) of porcine kidney-15 (PK-15) cells (300,000 cells/ml) in Eagle's Minimum Essential Medium was added to each serum per PRV sample. The samples were subsequently incubated at 37° C. for 2 days. Neutralizing titers represent the reciprocals of the highest dilutions which protected 50% of the cells from cytopathic effects.

Table 1 sets forth the protection of mice from challenge by virulent PRV by immunization with gp50 produced in vaccinia virus. Mice were immunized by tail scarification with 25 μl or by the footpad route with 50 μl. Mice were immunized 28 days prior to challenge (except mice given PR-Vac which were immunized 14 days prior to challenge).

TABLE 1

| Immunizing Agent | Dose (PFU) | Route | Neutralizing Titers[a] | % Survival[b] |
|---|---|---|---|---|
| gp50 | $3.0 \times 10^7$ | Tail | 1024 | 93 |
| gp50 | $6.0 \times 10^7$ | Footpad | 1024 | 100 |
| gp50 | $7.5 \times 10^6$ | Tail | 512 | 93 |
| vaccinia[c] | $7.5 \times 10^6$ | Tail | <8 | 27 |
| BME[d] | — | Tail | <8 | 20 |
| PR-Vac[e] | — | Footpad | 512 | 90 |

[a]Neutralizing titer against PRV at day of challenge (+ complement).
[b]Challenged with 10 LD50 of PRV Rice strain by intraperitoneal route.
[c]Control virus.
[d]Basal medium Eagle, negative control.
[e]Norden Laboratories, Lincoln, NE, inactivated PRV vaccine, positive control.

Table 2 sets forth the protection of mice from challenge by virulent PRV by immunization with gp50 produced in CHO cells. Mice were immunized at 28 days, 18 days and 7 days prior to challenge. Mice received preparations with adjuvants subcutaneously on the first dose and preparations in saline intraperitoneally on the second and third doses. Each mouse received $10^6$ disrupted cells/dose.

TABLE 2

| Immunizing Agent/Adjuvant | Neutralizing Titers[a] | % Survival[b] |
|---|---|---|
| gp50/CFA[c] | 512 | 100 (10/10) |
| gp50/CFA (2 doses) | ND | 80 (4/5) |
| gp50/IFA[d] | 1024 | 90 (9/10) |
| gp50/saline | 256 | 100 (3/3) |
| CHO-renin[e]/CFA | <8 | 10 (1/10) |
| Nontreated | <8 | 0 (0/10) |
| PR-Vac[f] | 4096 | 90 (9/10) |

[a]Neutralizing titer against PRV at day of challenge (+ complement).
[b]Challenged with 30 LD50 of PRV Rice strain by footpad route.
[c]Complete Freund's adjuvant.
[d]Incomplete Freund's adjuvant.
[e]Control cells expressing renin.
[f]Norden Laboratories, Lincoln, NE, inactivated PRV vaccine, positive control.

Table 3 sets forth the protection of swine from challenge by virulent PRV by immunization with gp50 produced in CHO cells. Swine were immunized at 21 days and 7 days prior to challenge. Swine received $2 \times 10^7$ disrupted cells per dose. The first dose was mixed with complete Freund's adjuvant while the second dose was suspended in saline. Both doses were given intramuscularly.

TABLE 3

| Immunizing Agent/Adjuvant | Geometric Mean Titer[a] | % Survival[b] |
|---|---|---|
| gp50/CFA | 25 | 100 |
| CHO-renin/CFA | <8 | 0 |

[a]Neutralizing titer against PRV at day of challenge.
[b]Challenge with PRV Rice strain $1 \times 10^5$ pfu/pig by the intranasal route.

These three tables demonstrate that gp50 can raise neutralizing antibodies and protect mice and swine from lethal PRV challenge.

In another aspect of the instant invention we produced a derivative of glycoprotein gp50 by removing the DNA coding for the C-terminal end of gp50. The resulting polypeptide has a deletion for the amino acid sequence necessary to anchor gp50 into the cell membrane. When expressed in mammalian cells this gp50 derivative is secreted into the medium. Purification of this gp50 derivative from the medium for use as a subunit vaccine is much simpler than fractionation of whole cells. Removal of the anchor sequence to convert a membrane protein into a secreted protein was first demonstrated for the influenza hemagglutinin gene (M.-J. Gething and J. Sambrook, Nature, 300, pp. 598–603 (1982)).

Referring now to Chart L, plasmid pDIE50 from above is digested with SalI and EcoRI. The 5.0 and 0.7 kb fragments are isolated. The 0.7 kb fragment encoding a portion of gp50 is digested with Sau3A and a 0.5 kb SalI/Sau3A fragment is isolated. To introduce a stop codon after the truncated gp50 gene, the following oligonucleotides are synthesized:

5' GATCGTCGGCTAGTGAGTAGGTAGG 3'
3' CAGCCGATCACTCATCCATCCTTAA 5'

The 5.0 kb EcoRI/SalI fragment, the 0.5 kb SalI/Sau3A fragment and the annealed oligonucleotides are ligated to produce plasmid pDIE50T. Digestion with EcoRI and SalI produces a 580 bp fragment. pDIE50T is cut with EcoRI and the 0.6 kb EcoRI fragment containing the bGH polyA site (fragment 12) is cloned in to produce plasmid pDIE50TPA. Digestion of pDIE50TPA with BamHI and PvuII yields a 970 bp fragment when the polyadenylation signal is in the proper orientation. pDIE50TPA is used to transfect CHO dhfr⁻ cells. Selected dhfr⁺ CHO cells produce a truncated form of gp50 which is secreted into the medium as detected by labelling with $^{35}$S-methionine and immunoprecipitation.

EXAMPLE 3

In this example we set forth the isolation, cloning and sequencing of the gp63 and gI genes.

1. Library Construction

PRV genomic DNA was prepared as described previously (T. J. Rea, et al., supra.). Fragments of 0.5–3.0 kb were obtained by sonicating the PRV genomic DNA of the PRV Rice strain twice for 4 sec each time at setting 2 with a Branson 200 sonicator. After blunt ending the fragments with T4 DNA polymerase, the fragments were ligated to kinased EcoRI linkers (T. Maniatis, et al., supra). After over-digestion with EcoRI (since PRV DNA does not contain an EcoRI site, methylation was unnecessary), excess linkers were removed by agarose gel electrophoresis. The PRV DNA fragments in the desired size range were eluted by the glass slurry method, (B. Vogelstein and D. Gillespie, Proc. Natl. Acad. Sci. USA, 76, pp. 615–19 (1979)). A library of 61,000 λ/PRV recombinants (λPRVs) was constructed by ligating 500 ng of PRV DNA fragments to 750 ng of EcoRI digested λgt11 (R. A. Young and R. W. Davis, supra.) DNA in 50 mM Tris (pH 7.4), 10 mM MgCl₂, 10 mM dithiothreitol, 1 mM spermidine, 1 mM ATP, 400 units of T4 DNA ligase (New England Biolabs), in a final volume of 10 μl. The ligated DNA was packaged into bacteriophage λ virions using the Packagene extract (Promega Biotec, Madison, Wis.).

2. λPRV Library Screening

The λPRV library was screened as previously described (J. G. Timmins, et al., supra.; R. A. Young and R. W. Davis, supra.). 20,000 phages were screened per 150 mm LB-ampicillin plate. The screening antisera were raised by injecting mice with size fractions of PRV infected cell proteins (ICP's) eluted from SDS-polyacrylamide gels (J. G. Timmins, et al., supra.). Plaques giving positive signals upon screening with antisera were picked from the agar plates with a sterile pasteur pipette, resuspended in 1 ml SM buffer (T. Maniatis, et al., supra) and rescreened. The screening was repeated until the plaques were homogeneous in reacting positively.

Approximately 43,000 λPRV recombinants were screened with mouse antisera to PRV infected Vero cell proteins, isolated from SDS-polyacrylamide gels. Sixty positive λPRV phages were isolated.

3. Phage Stock Preparation

High titer phage stocks ($10^{10}$–$10^{11}$ pfu/ml) were prepared by the plate lysate method (T. Maniatis et al., supra). A single, well-isolated positive signal plaque was picked and resuspended in 1 ml SM. 100 μl of the suspension was adsorbed to 300 μl of E. coli Y1090 (available from the American Type Culture Collection (ATCC), Rockville, Md.) at 37° C. for 15 min, diluted with 10 ml LB-top agarose, poured evenly on a 150 mm LB-ampicillin plate and incubated overnight at 42° C. The top agarose was gently scraped off with a flamed glass slide and transferred to a 30 ml Corex tube. 8 ml of SM and 250 μl of chloroform were added, mixed and incubated at 37° C. for 15 min. The lysate was clarified by centrifugation at 10,000 rpm for 30 min in the HB-4 rotor. The phage stock was stored at 4° C. with 0.3% chloroform.

4. Fusion Protein Preparation and Analysis

LB medium (Maniatis, et al., supra.) was inoculated 1:50 with a fresh overnight culture of E. coli K95 (sup$^-$, λ$^-$, gal$^-$, str$^r$, nusA$^-$; D. Friedman, supra.) and grown to an $OD_{550}$= 0.5 at 30° C. 25 ml of culture was infected with λPRV phage at a multiplicity of 5 and incubated in a 42° C. shaking water bath for 25 min, followed by transfer to 37° C. for 2–3 hours. The cells were pelleted at 5,000 rpm for 10 min in the HB-4 rotor and resuspended in 100 μl of 100 mM Tris (pH 7.8), 300 mM NaCl. An equal volume of 2× SDS-PAGE sample buffer was added, and the sample was boiled for 10 min. 5 μl of each sample was analyzed by electrophoresis on analytical SDS-polyacrylamide gels as described in L. Morse et al., J. Virol, 26, pp. 389–410 (1978).

The fusion polypeptide preparations were scaled up 10-fold for mouse injections. The β-galactosidase/PRV fusion polypeptides were isolated after staining a strip of the gel with coomassie blue (L. Morse et al., supra; K. Weber and M. Osborn, in The Proteins, 1, pp. 179–223 (1975)). Fusion polypeptide quantities were estimated by analytical SDS-PAGE. Cell lysates from λPRV infected E. coli K95 cultures were electrophoresed in 9.25% SDS-polyacrylamide gels. Overproduced polypeptide bands with molecular weights greater than 116,000 daltons, absent from λgt11-infected controls, were β-galactosidase-PRV fusion polypeptides. The p-galactosidase-PRV fusion polypeptides ranged in size from 129,000 to 158,000 daltons. Approximately 50–75 μg of fusion polypeptide was resuspended in complete Freund's adjuvant and injected subcutaneously and interperitoneally per mouse. Later injections were done intraperitoneally in incomplete Freund's adjuvant.

5. Antisera Analysis

Immunoprecipitations of $^{14}$C-glucosamine ICP's, $^{35}$S-methionine ICP's and $^{14}$C-glucosamine gX were done as previously described (T. J. Rea, et al., supra.). These techniques showed that gp63 and gI had been isolated in a λgt11 recombinant phage. We called these phages λ37 and λ36 (gp63) and λ23 (gI).

6. λDNA Mini-preps

Bacteriophage were rapidly isolated from plate lysates (T. J. Silhavy et al., Experiments With Gene Fusions, (1984)). 5% and 40% glycerol steps (3 ml each in SM buffer) were layered in an SW41 tube. A plate lysate (~6 ml) was layered and centrifuged at 35,000 rpm for 60 min at 4° C. The supernatant was discarded and the phage pellet was resuspended in 1 ml SM. DNAse I and RNAse A were added to final concentrations of 1 μg/ml and 10 μg/ml. After incubation at 37° C. for 30 min, 200 μl of SDS Mix (0.25 M EDTA, 0.5 M Tris (pH 7.8), 2.5% SDS) and proteinase K (to 1 mg/ml) were added and incubated at 68° C. for 30 min. The λDNA was extracted with phenol three times, extracted with chloroform, and ethanol precipitated. An average 150 mm plate lysate yields 5–10 μg of λDNA.

7. λPRV DNA Analysis

PRV DNA was digested to completion with BamHI and KpnI, electrophoresed in 0.8% agarose and transferred to nitrocellulose by the method of Southern (J. Mol. Biol., 98, pp. 503–17 (1975)). The blots were sliced into 4 mm strips and stored desiccated at 20–25°. λPRV DNAs were nick-translated (Amersham) to specific activities of approximately $10^8$ cpm/μg. Pre-hybridization was done in 6× SSC, 30% formamide, 1× Denhardt's reagent (0.02% each of ficoll, polyvinylpyrrolidone and bovine serum albumin), 0.1% SDS, 50 μg/ml heterologous DNA at 70° C. for 1 hour. Hybridization was done in the same solution at 70° C. for 16 hours. Fifteen minute washes were done twice in 2× SSC, 0.1% SDS and twice in 0.1× SSC, and 0.1% SDS, all at 20–25°. The blots were autoradiographed with an intensifying screen at ~70° C. overnight.

By Southern blotting the PRV glycoprotein genes contained in λ23, λ36 and λ37 mapped to the BamHI 7 fragment in the unique small region (see T. J. Rea, et al., supra.). Finer mapping of this fragment showed that λ23 (gI) gene mapped distal to the gX gene and that λ37 mapped to the internal region of BamHI 7, as shown in Chart D.

8. Sequencing the gp63 and gI Genes

The PRV DNA in λ36 and λ37 was determined to contain a StuI cleavage site. There is only one StuI cleavage site in the BamHI 7 fragment; therefore, the open reading frame that included the StuI cleavage site was sequenced. Chart E shows various restriction enzyme cleavage sites located in the gp63 gene and flanking regions. BamHI 7 was subcloned and digested with these restriction enzymes. Each of the ends generated by the restriction enzymes was labeled with γ-$^{32}$P-ATP using polynucleotide kinase and sequenced according to the method of Maxam and Gilbert, Methods Enzymol., 65, 499–560 (1980).

Plasmid pPR28 is produced by cloning the BamHI 7 fragment isolated from pUC1129 into plasmid pSV2 gpt (R. C. Mulligan and P. Berg, Proc. Natl. Acad. Sci. USA, 78, pp. 2072–76 (1981)).

Plasmid pPR28-1 was produced by digesting pPR28 with PvuII and then recircularizing the piece containing the E. coli origin of replication and bla gene to produce a plasmid comprising a 4.9 kb PvuII/BamHI 7 PRV fragment containing the DNA sequence for gI.

Chart N shows various restriction enzyme cleavage sites located in the gI gene and flanking regions. BamHI 7 was subcloned, digested, labeled and sequenced as set forth above.

The DNA sequences for glycoproteins gp63 and gI are set forth in Charts B and C respectively. This DNA may be employed to detect animals actively infected with PRV. For example, one could take a nasal or throat swab, and then by standard DNA/DNA hybridization methods detect the presence of PRV.

EXAMPLE 4

In this example we set forth the expression of gI in mammalian cells.

A BamHI 7 fragment containing the gI gene is isolated from plasmid pPR28 (see above) by digesting the plasmid with BamHI, separating the fragments on agarose gel and then excising the fragment from the gel.

Referring now to Chart O, the BamHI 7 fragment isolated above is then cloned into plasmid pUC19 (purchased from Pharmacia/PL) to produce plasmid A. Plasmid A is digested with DraI. DraI cleaves the pUC19 sequence in several places, but only once in the BamHI 7 sequence between the gp63 and gI genes (Chart D) to produce, inter alia, fragment 1. BamHI linkers are ligated onto the DraI ends of the fragments, including fragment 1, and the resulting fragment mixture is digested with BamHI. The product fragments are separated by agarose gel electrophoresis and fragment 2 (2.5 kb) containing the gI gene is purified. Fragment 2 is cloned into pUC19 digested with BamHI to produce plasmid pUCD/B. Of the two plasmids so produced, the plasmid containing the gI gene in the proper orientation is determined by digesting the plasmids with BsmI and EcoRI; the plasmid in the proper orientation contains a characteristic 750 bp BsmI/EcoRI fragment.

Referring now to Chart P, plasmid pUCD/B (Chart O) is digested with BsmI and EcoRI and the larger fragment (fragment 3, 4.4 kb) is purified by agarose gel electrophoresis. The following two oligonucleotides are synthesized chemically by well-known techniques or are purchased from a commercial custom synthesis service:

5' CGCCCCGCTTAAATACCGGGAGAAG 3'

5' AATTCTTCTCCCGGTATTTAAGCGGGGCGGG 3'

These oligonucleotides are ligated to fragment 3 to replace the coding sequence for the C-terminus of the gI gene which was deleted by the BsmI cleavage. The resulting plasmid, pGI, contains a complete coding region of the gI gene with a BamHI cleavage site upstream and an EcoRI cleavage site downstream from the gI coding sequences.

Plasmid pGI is digested with EcoRI and BamHI and a 1.8 kb fragment comprising the gI gene (fragment 4) is purified on an agarose gel.

Plasmid pSV2dhfr, (supra.) is cut with EcoRI, and is then cut with BamHI to produce fragment 5 (5.0 kb) containing the dhfr marker, which is isolated by agarose gel electrophoresis. Then fragments 4, and 5 are ligated to produce plasmid pDGI which comprises the dihydrofolate reductase and ampicillin resistance markers, the SV40 promoter and origin of replication, and the gI gene.

Referring now to Chart Q, the immediate early promoter from human cytomegalovirus Towne strain is added upstream from the gI gene. Plasmid pDGI is digested with BamHI to produce fragment 6. The human cytomegalovirus (Towne) immediate early promoter is isolated (supra.) to produce fragment 7. Fragments 6 and 7 are then ligated to produce plasmid pDIEGIdhfr. To confirm that the promoter is in the proper orientation the plasmid is digested with SacI and BstEII restriction enzymes. The production of an about 400 bp fragment indicates proper orientation.

A 0.6 kb PvuII/EcoRI fragment containing the bovine growth hormone polyadenylation signal is isolated from the plasmid pSVCOW7 (supra.) to produce fragment 8. Fragment 8 is cloned across the SmaI/EcoRI sites of pUC9 (supra.) to produce plasmid pCOWT1. pCOWT1 is cut with SalI, treated with T4 DNA polymerase, and EcoRI linkers are ligated on. The fragment mixture so produced is then digested with EcoRI and a 0.6 kb fragment is isolated (fragment 9). Fragment 9 is cloned into the EcoRI site of pUC19 to produce plasmid pCOWT1E. pCOWT1E is digested with EcoRI to produce fragment 10 (600 bp).

Plasmid pDIEGIdhfr is digested with EcoRI and ligated with fragment 10 containing the bGH polyadenylation signal to produce plasmid pDIEGIPA. The plasmid having the gI gene in the proper orientation is demonstrated by the production of a 1400 bp fragment upon digestion with BamHI and BstEII.

The resulting plasmid is transfected into dhfr⁻ Chinese hamster ovary cells and dhfr⁺ cells are selected to obtain cell lines expressing gI (Subramani, et al, Mol. Cell Biol., 1, pp.854–64 (1981)). The expression of gI is amplified by selecting clones of transfected cells that survive growth in progressively higher concentrations of methotrexate (McCormick, et al, Mol. Cell Biol., 4, pp. 166–72 (1984).

EXAMPLE 5

In this example we set forth the expression of gp63 in mammalian cells.

The BamHI 7 fragment of PRV DNA (supra.) is isolated from pPRXh1 [NRRL B-15772], and subcloned into the BamHI site of plasmid pBR322 as in Example 1 for use in sequencing and producing more copies of the gp63 gene.

Referring now to Chart R, from within BamHI 7 a 1.9 kb BstEII/KpnI fragment (fragment 1) is subcloned by cutting BamHI 7 with BstEII, treating the ends with T4 DNA polymerase, and then cutting with KpnI. Fragment 1 is isolated and cloned between the KpnI and SmaI sites in pUC19 (purchased from Pharmacia/PL, Piscataway, N.J.) to yield plasmid pPR28-1BK.

Plasmid pPR28-1BK is cut with DraI plus MaeIII to yield fragment 2 (1.1 kb). The DraI cleavage site is outside the coding region of the gp63 gene and downstream from its polyadenylation signal. The MaeIII cleavage site cuts 21 bases downstream from the ATG initiation codon of the gp63 gene. To replace the coding region removed from the gp63 gene, the following two oligonucleotides are synthesized chemically or purchased from commercial custom synthesis services (fragment 4):

5' GATCCGCAGTACCGGCGTCGATGAT-
GATGGTGGCGCGCGAC 3'

3' GCGTCATGGCCGCAGCTACTACTACCAC-
CGCGCGCTGCACTG 5'

Plasmid pSV2dhfr, supra., is cut with EcoRI, treated with T4 DNA polymerase, then cut with BamHI and the larger (5.0 kb) fragment is isolated to produce fragment 4 containing the dhfr marker. Then fragments 2, 3, and 4 are ligated to produce plasmid pGP63dhfr.

Referring now to Chart S, the immediate early promoter from human cytomegalovirus Towne strain is added upstream from the gp63 gene. pGP63dhfr is digested with BamHI and treated with bacterial alkaline phosphatase to produce fragment 5. A 760 bp Sau3A fragment containing human cytomegalovirus (Towne) immediate early promoter is isolated to produce fragment 6. These fragments are then ligated to produce plasmid pIEGP63dhfr. To confirm that the promoter is in the proper orientation the plasmid is digested with SacI and PvuII and a 150 bp fragment is produced.

The resulting plasmid is transfected into dhfr⁻ Chinese hamster ovary cells and dhfr⁺ cells are selected to obtain cell lines expressing gp63. Since the levels of synthesis of $gp^{63}$ by this system were too low to detect by the methods we used, we produced the polypeptide in vaccinia virus as set forth below.

EXAMPLE 6

In this example we set forth the expression of gp63 in vaccinia virus. The method used herein incorporates aspects of other syntheses referred to above.

Fragments 1, 2, 3, and 4 are produced according to Example 5.

Plasmid pGS20 (Mackett, et al., J. Virol., 49, pp. 857–64 (1984)) is cut with BamHI and SmaI, and the larger 6.5 kb fragment is isolated by gel electrophoresis. Fragment 2, the oligonucleotides, and the pGS20 fragment are ligated together to produce plasmid pVV63. This plasmid is transfected into CV-1 cells (ATCC CCL 70) infected with the WR strain of vaccinia virus (ATCC VR-119), selected for thymidine kinase negative recombinants by plating on 143 cells (ATCC CRL 8303) in BUdR by the methods described by Mackett, et al. in DNA Cloning, Volume II: A Practical Approach, D. M. Glover, ed., IRL Press, Oxford (1985). The resulting virus, vaccinia-gp63, expresses gp50 in infected cells, as assayed by labelling of the proteins of the infected cell with $^{14}$C-glucosamine and immunoprecipitation with anti-gp63 antiserum.

The BamHI/EcoRI fragment from plasmid pGI, the DraI/MaeIII fragment from plasmid pPR28-1BK, or the BamHI/MaeIII fragment from pBGP50-23 all described above, may also be treated with Bal31 and inserted in pTRZ4 (produced as set forth in copending U.S. patent application Ser. No. 606,307) as described in Rea, et al., supra., and used to transform E. coli. By this method, gp50, gp63, and gI can be produced as a fusion protein in E. coli.

Also, by substituting, for example, pSV2neo (available from the American Type Culture Collection) for pSV2dhfr in the above example, the recombinant plasmid comprising the PRV glycoprotein gene could be transformed into other host cells. Transformed cells would be selected by resistance to antibiotic G418 which is encoded by the plasmid.

One can also express the polypeptides of the instant invention in insect cells as follows: By putting a BamHI linker on the EcoRI site of pD50 and digestion with BamHI, or putting a BamHI linker on the EcoRI site of pGP63dhfr and digestion with BamHI, or by digestion of pUCD/B with BamHI, one obtains BamHI fragments containing the gp50, gp63, or gI genes respectively. These BamHI fragments can be cloned into a BamHI site downstream from a polyhedrin promoter in pAC373 (Mol. Cell. Biol., 5, pp. 2860–65 (1985)). The plasmids so produced can be co-transfected with DNA from baculovirus Autographa californica into Sf9 cells, and recombinant viruses isolated by methods set forth in the article. These recombinant viruses produce gp50, gp63, or gI upon infecting Sf9 cells.

A vaccine prepared utilizing a glycoprotein of the instant invention or an immunogenic fragment thereof can consist of fixed host cells, a host cell extract, or a partially or completely purified PRV glycoprotein preparation from the host cells or produced by chemical synthesis. The PRV glycoprotein immunogen prepared in accordance with the present invention is preferably free of PRV virus. Thus, the vaccine immunogen of the invention is composed substantially entirely of the desired immunogenic PRV polypeptide and/or other PRV polypeptides displaying PRV antigenicity.

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents including aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Another suitable adjuvant is Freund's Incomplete Adjuvant (Difco Laboratories, Detroit, Michigan).

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, the concentration of the immunogen can range from about 1.0 μg to about 100 mg per pig. A preferable range is from about 100 μg to about 3.0 mg per pig. A suitable dose size is about 1–10 ml, preferably about 1.0 ml. Accordingly, a dose for intramuscular injection, for example, would comprise 1 ml containing 1.0 mg of immunogen in admixture with 0.5% aluminum hydroxide. Comparable dose forms can also be prepared for parenteral administration to baby pigs, but the amount of immunogen per dose will be smaller, for example, about 0.25 to about 1.0 mg per dose.

For vaccination of sows, a two dose regimen can be used. The first dose can be given from about several months to about 5 to 7 weeks prior to farrowing. The second dose of the vaccine then should be administered some weeks after the first dose, for example, about 2 to 4 weeks later, and vaccine can then be administered up to, but prior to, farrowing. Alternatively, the vaccine can be administered as a single 2 ml dose, for example, at about 5 to 7 weeks prior to farrowing. However, a 2 dose regimen is considered preferable for the most effective immunization of the baby pigs. Semi-annual revaccination is recommended for breeding animals. Boars may be revaccinated at any time. Also, sows can be revaccinated before breeding. Piglets born to unvaccinated sows may be vaccinated at about 3–10 days, again at 4–6 months and yearly or preferably semi-annually thereafter.

The vaccine may also be combined with other vaccines for other diseases to produce multivalent vaccines. It may also be combined with other medicaments, for example, antibiotics. A pharmaceutically effective amount of the vaccine can be employed with a pharmaceutically acceptable carrier or diluent to vaccinate animals such as swine, cattle, sheep, goats, and other mammals.

Other vaccines may be prepared according to methods well known to those skilled in the art as set forth, for example, in I. Tizard, An Introduction to Veterinary Immunology, 2nd ed. (1982), which is incorporated herein by reference.

As set forth above, commercial vaccine PRV's have been found to have the gI and gp63 genes deleted. Therefore gI and gp63 polypeptides produced by the methods of this invention can be used as diagnostic agents to distinguish between animals vaccinated with these commercial vaccines and those infected with virulent virus.

To differentiate between infected and vaccinated animals, one could employ, for example, an ELISA assay. gI or gp63 protein, produced, for example, in E. coli by recombinant DNA techniques (Rea, et al., supra.), is added to the wells of suitable plastic plates and allowed sufficient time to absorb to the plastic (e.g., overnight, 20–25° C.). The plates are washed and a blocking agent (e.g., BSA) is added to neutralize any unreacted sites on the plastic surface. A wash follows and then the pig serum is added to the wells. After about 1 hour incubation at 20–25° C., the wells are washed and a protein A-horseradish peroxidase conjugate is added to each well for an about 1 hour incubation a 20–25° C. Another wash follows and the enzyme substrate (o-phenylenediamine) is added to the wells and the reaction is terminated with acid. Absorbency is measured at 492 nanometers to quantitate the amount of gI or gp63 antibody present in the serum. Lack of gI or gp63 indicates that an animal is not infected. By testing for other PRV antigens, one could establish whether or not a given animal was vaccinated.

CHART A.

```
                                    27                                  54
ATG CTG CTC GCA GCG CTA TTG GCG GCG CTG GTC GCC CGG ACG ACG CTC GGT GCG
Met Leu Leu Ala Ala Leu Leu Ala Ala Leu Val Ala Arg Thr Thr Leu Gly Ala 81                                 108
GAC GTG GAC GCC GTG CCC GCG CCG ACC TTC CCC CCG CCC GCG TAC CCG TAC ACC
Asp Val Asp Ala Val Pro Ala Pro Thr Phe Pro Pro Pro Ala Tyr Pro Tyr Thr 135                                 162
GAG TCG TGG CAG CTG ACG CTG ACG ACG GTC CCC TCG CCC TTC GTC GGC CCC GCG
Glu Ser Trp Gln Leu Thr Leu Thr Thr Val Pro Ser Pro Phe Val Gly Pro Ala 189                                 216
GAC GTC TAC CAC ACG CGC CCG CTG GAG GAC CCG TGC GCG GTG GTG GCG CTG ATC
Asp Val Tyr His Thr Arg Pro Leu Glu Asp Pro Cys Gly Val Val Ala Leu Ile 243                                 270
TCC GAC CCG CAG GTG GAC CGG CTG CTG AAC GAG GCG GTG GCC CAC CGG CGG CCC
Ser Asp Pro Gln Val Asp Arg Leu Leu Asn Glu Ala Val Ala His Arg Arg Pro 297                                 324
ACG TAC CGC GCC CAC GTG GCC TGG TAC CGC ATC GCG GAC GGG TGC GCA CAC CTG
Thr Tyr Arg Ala His Val Ala Trp Tyr Arg Ile Ala Asp Gly Cys Ala His Leu 351                                 378
CTG TAC TTT ATC GAG TAC GCC GAC TGC GAC CCC AGG CAG GTC TTT GGG CGC TGC
Leu Tyr Phe Ile Glu Tyr Ala Asp Cys Asp Pro Arg Gln Val Phe Gly Arg Cys 405                                 432
CGG CGC CGC ACC ACG CCG ATG TGG TGG ACC CCG TCC GCG GAC TAC ATG TTC CCC
Arg Arg Arg Thr Thr Pro Met Trp Trp Thr Pro Ser Ala Asp Tyr Met Phe Pro 459                                 486
ACG GAG GAC GAG CTG GGG CTG CTC ATG GTG GCC CCG GGG CGG TTC AAC GAG GGC
Thr Glu Asp Glu Leu Gly Ley Leu Met Val Ala Pro Gly Arg Phe Asn Glu Gly 513                                 540
CAG TAC CGG CGC CTG GTG TCC CTC GAC GGC GTG AAC ATC CTC ACC GAC TTC ATG
Gln Tyr Arg Arg Leu Val Ser Val Asp Gly Val Asn Ile Leu Thr Asp Phe Met 567                                 594
GTG GCG CTC CCC GAG GGG CAA GAG TGC CCG TTC GCC CGC GTG GAC CAG CAC CGC
Val Ala Leu Pro Glu Gly Gln Glu Cys Pro Phe Ala Arg Val Asp Gln His Arg 621                                 648
ACG TAC AAG TTC GGC GCG TGC TGG AGC GAC GAC AGC TTC AAG CGG GGC GTG GAC
Thr Tyr Lys Phe Gly Ala Cys Trp Ser Asp Asp Ser Phe Lys Arg Gly Val Asp 675                                 702
GTG ATG CGA TTC CTG ACG CCG TTC TAC CAG CAG CCC CCG CAC CGG GAG GTG GTG
Val Met Arg Phe Leu Thr Pro Phe Tyr Gln Gln Pro Pro His Arg Glu Val Val 729                                 756
AAC TAC TGG TAC CGC AAG AAC GGC CGG ACG CTC CCG CGG GCC CAC GCC GCC GCC
Asn Tyr Trp Tyr Arg Lys Asn Gly Arg Thr Leu Pro Arg Ala His Ala Ala Ala 783                                 810
ACG CCG TAC GCC ATC GAC CCC GCG CGG CCC TCG GCG GGC TCG CCG AGG CCC CGG
Thr Pro Tyr Ala Ile Asp Pro Ala Arg Pro Ser Ala Gly Ser Pro Arg Pro Arg 837                                 864
CCC CGG CCC CGG CCC CGG CCC CGG CCG AAG CCC GAG CCC GCC CCG GCG ACG CCC
Pro Arg Pro Arg Pro Arg Pro Arg Pro Lys Pro Glu Pro Ala Pro Ala Thr Pro 891                                 918
GCG CCC CCC GAC CGC CTG CCC GAG CCG GCG ACG CGG GAC CAC GCC GCC GGG GGC
Ala Pro Pro Asp Arg Ceu Pro Glu Pro Ala Thr Arg Asp His Ala Ala Gly Gly
```

```
                                 945                                    972
CGC CCC ACG CCG CGA CCC CCG AGG CCC GAG ACG CCG CAC CGC CCC TTC GCC CCG
Arg Pro Thr Pro Arg Pro Pro Arg Pro Glu Thr Pro His Arg Pro Phe Ala Pro 999                                   1026
CCG GCC GTC GTG CCC AGC GGG TGG CCG CAG CCC GCG GAG CCG TTC CAG CCG CGG
Pro Ala Val Val Pro Ser Gly Trp Pro Gln Pro Ala Glu Pro Phe Gln Pro Arg 1053                                   1080
ACC CCC GCC GCG CCG GGC GTC TCG CGC CAC CGC TCG GTG ATC GTC GGC ACG GGC
Thr Pro Ala Ala Pro Gly Val Ser Arg His Arg Ser Val Ile Val Gly Thr Gly 1107                                   1134
ACC GCG ATG GGC GCG CTC CTG GTG GGC GTG TGC GTC TAC ATC TTC TTC CGC CTG
Thr Ala Met Gly Ala Leu Leu Val Gly Val Cys Val Tyr Ile Phe Phe Arg Leu 1161                                   1188
AGG GGG GCG AAG GGG TAT CGC CTC CTG GGC GGT CCC GCG GAC GCC GAC GAG CTA
Arg Gly Ala Lys Gly Tyr Arg Leu Leu Gly Gly Pro Ala Asp Ala Asp Glu Leu

1215
AAA GCG CAG CCC GGT CCG TAG
Lys Ala Gln Pro Gly Pro

CHART B.
                                  27                                     54
ATG ATG ATG GTG GCG CGC GAC GTG ACC CGG CTC CCC GCG GGG CTC CTC CTC GCC
Met Met Met Val Ala Arg Asp Val Thr Arg Leu Pro Ala Gly Leu Leu Leu Ala 81                                    108
GCC CTG ACC CTG GCC GCC CTG ACC CCG CGC GTC GGG GGC GTC CTC TTC AGG GGC
Ala Leu Thr Leu Ala Ala Leu Thr Pro Arg Val Gly Gly Val Leu Phe Arg Gly 135                                    162
GCC GGC GTC AGC GTG CAC GTC GCC GGG AGC GCC GTC CTC GTG CCC GGC GAC GCG
Ala Aly Val Ser Val His Val Ala Gly Ser Ala Val Leu Val Pro Gly Asp Ala 189                                    216
CCC AAC CTG ACG ATC GAC GGG ACG CTG CTG TTT CTG GAG GGG CCC TCG CCG AGC
Pro Asn Leu Thr Ile Asp Gly Thr Leu Leu Phe Leu Glu Gly Pro Ser Pro Ser 243                                    270
AAC TAC AGC GGG CGC GTG GAG CTG CTG CGC CTC GAC CCC AAG CGC GCC TGC TAC
Asn Tyr Ser Gly Arg Val Glu Leu Leu Arg Leu Asp Pro Lys Arg Ala Cys Tyr 297                                    324
ACG CGC GAG TAC GCC GCC GAG TAC GAC CTC TGC CCC CGC GTG CAC CAC GAG GCC
Thr Arg Glu Tyr Ala Ala Glu Tyr Asp Leu Cus Pro Arg Val His His Glu Ala 351                                    378
TTC CGC GGC TGT CTG CGC AAG CGC GAG CCG CTC GCC CGG CGC GCG TCC GCC GCG
Phe Arg Gly Cus Leu Arg Lus Arg Glu Pro Leu Ala Arg Arg Ala Ser Ala Ala 405                                    432
GTG GAG GCG CGC CGG CTG CTG TTC GTC TCG CGC CCG GCC CCG CCG GAC GCG GGG
Val Glu Ala Arg Arg Leu Leu Phe Val Ser Arg Pro Ala Pro Pro Asp Ala Gly 459                                    486
TCG TAC GTG CTG CGG GTC CGC GTG AAC GGG ACC ACG GAC CTC TTT GTG CTG ACG
Ser Tyr Val Leu Arg Val Arg Val Asn Gly Thr Thr Asp Leu Phe Val Leu Thr 513                                    540
GCC CTG GTG CCG CCC AGG GGG CGC CCC CAC CAC CCC ACG CCG TCG TCC GCG GAC
Ala Leu Val Pro Pro Arg Gly Arg Pro His His Pro Thr Pro Ser Ser Ala Asp 567                                    594
GAG TGC CGG CCT GTC GTC GGA TCG TGG CAC GAC AGC CTG CGC GTC GTG GAC CCC
Glu Cys Arg Pro Val Val Gly Ser Trp his Asp Ser Leu Arg Val Val Asp Pro 621                                    648
GCC GAG GAC GCC GTG TTC ACC ACG CCG CCC CCG ATC GAG CCA GAG CCG CCG ACG
Ala Glu Asp Ala Val Phe Thr Thr Pro Pro Pro Ile glu Pro Glu Pro Pro Thr
```

```
                                  675                                           702
ACC CCC GCG CCC CCC CGG GGG ACC GGC GCC ACC CCC GAG CCC CGC TCC GAC GAA
Thr Pro Ala Pro Pro Arg Gly Thr Gly Ala Thr Pro Gly Pro Arg Ser Asp Glu 729                                           756
GAG GAG GAG GAC GAG GAG GGG GCG ACG ACG GCG ATG ACC CCG GTG CCC GGG ACC
Glu Glu Glu Asp Glu Glu Gly Ala Thr Thr Ala Met Thr Pro Val Pro Gly Thr 783                                           810
CTG GAC GCG AAC GGC ACG ATG GTG CTG AAC GCC AGC GTC GTG TCG CGC GTC CTG
Leu Asp Ala Asn Gly Thr Met Val Ley Asn Ala Ser Val Val Ser Arg Val Leu 837                                           864
CTC GCC GCC GCC AAC GCC ACG GCG GGC GCC CGG GGC CCC GGG AAG ATA GCC ATG
Leu Ala Ala Ala Asn Ala Thr Ala Gly Ala Arg Gly Pro Gly Lys Ile Ala Met 891                                           918
GTG CTG GGG CCC ACG ATC GTC GTC CTC CTG ATC TTC TTG GGC GGG GTC GCC TGC
Val Leu Gly Pro Thr Ile Val Val Leu Leu Ile Phe Leu Gly Gly Val Ala Cys 945                                           972
GCG GCC CGG CGC TGC GCG CGC GGA ATC GCA TCT ACC GGC CGC GAC CCG GGC GCG
Ala Ala Arg Arg Cys Ala Arg Gly Ile Ala Ser Thr Gly Arg Asp Pro Gly Ala 999                                          1026
GCC CGG CGG TCC ACG CGC CGC CCC CGC GGC GCC CGC CCC CCA ACC CCG TCG CCG
Ala Arg Arg Ser Thr Arg Arg Pro Arg Gly Ala Arg Pro Pro Thr Pro Ser Pro

1053
GGG CGC CCG TCC CCC AGC CCA AGA TGA
Gly Arg Pro Ser Pro ser Pro Arg

CHART C.
                                  27                                            54
ATG CGG CCC TTT CTG CTG CGC GCC GCG CAG CTC CTG GCG CTG CTG GCC CTG GCG
Met Arg Pro Phe Ley Leu Arg Ala Ala Gln Leu Leu Ala Leu Leu Ala Leu Ala 81                                            108
CTC TCC ACC GAG GCC CCG AGC CTC TCC GCC GAG ACG ACC CCG GGC CCC GTC ACC
Leu Ser Thr Glu Ala Pro Ser Leu Ser Ala Glu Thr Thr Pro Gly Pro Val Thr 135                                           162
GAG GTC CCG AGT CCC TCG GCC GAG GTC TGG GAC CTC TCC ACC GAG GCC GGC GAC
Glu Val Pro Ser Pro Ser Ala Glu Val Trp Asp Leu Ser Thr Glu Ala Gly Asp 189                                           216
GAT GAC CTC GAC GGC GAC CTC AAC GGC GAC GAC CGC CGC GCG GGC TTC GGC TCG
Asp Asp Leu Asp Gly Asp Leu Asn Gly Asp Asp Arg Arg Ala Gly Phe Gly Ser 243                                           270
GCC CTC GCC TCC CTG AGG GAG GCA CCC CCG GCC CAT CTG GTG AAC GTG TCC GAG
Ala Leu Ala Ser Leu Arg Glu Ala Pro Pro Ala His Leu Val Asn Val Ser Glu 297                                           324
GGC GCC AAC TTC ACC CTC GAC GCG CGC GGC GAC GGC GCC GTG GTG GCC GGG ATC
Gly Ala Asn Phe Thr Leu Asp Ala Arg Gly Asp Gly Ala Val Val Ala Gly Ile 351                                           378
TGG ACG TTC CTG CCC GTC CGC GGC TGC GAC GCC GTG GCG GTG ACC ATG GTG TGC
Trp Thr Phe Leu Pro Val Arg Gly Cus Asp Ala Val Ala Val Thr Met Val Cys 405                                           432
TTC GAG ACC GCC TGC CAC CCG GAC CTG GTG CTG GGC CGC GCC TGC GTC CCC GAG
Phe Glu Thr Ala Cys His Pro Asp Leu Val Leu Gly arg Ala Cys Val Pro Glu 459                                           486
GCC CCG GAG CGG GGC ATC GGC GAC TAC CTG CCG CCC GAG GTG CCG CGG CTC CAG
Ala Pro Glu Arg Gly Ile Gly Asp Tyr Leu Pro Pro Glu Val Pro Arg Leu Gln 513                                           540
CGC GAG CCG CCC ATC GTC ACC CCG GAG CGG TGG TCG CCG CAC CTG ACC GTC CGG
Arg Glu Pro Pro Ile Val Thr Pro Glu Arg TRp Ser Pro His Leu Thr Val Arg 567                                           594
CGG GCC ACG CCC AAC GAC ACG GGC CTC TAC ACG CTG CAC GAC GCC TCG GCG CCG
Arg Ala Thr Pro Asn Asp Thr Gly Leu Tyr Thr Leu His Asp Ala Ser Gly Pro
```

-continued

```
                        621                                                    648
CGG GCC GTG TTC TTT GTG GCG GTG GGC GAC CGG CCG CCC GCG CCG CTG GCC CCG
Arg Ala Val Phe Phe Val Ala Val Gly Asp Arg Pro Pro Ala Pro Leu Ala Pro 675                                                    702
GTG GGC CCC GCG CGC CAC GAG CCC CGC TTC CAC GCG CTC GGC TTC CAC TCG CAG
Val Gly Pro Ala Arg His Glu Pro Arg Phe His Ala Leu Gly Phe His Ser Gln 729                                                    756
CTC TTC TCG CCC GGG GAC ACG TTC GAC CTG ATG CCG CGC GTG GTC TCG GAC ATG
Leu Phe ser Pro Gly Asp Thr Phe Asp Leu Met Pro Arg Val Val Ser Asp Met 783                                                    810
GGC GAC TCG CGC GAG AAC TTC ACC GCC ACG CTG GAC TGG TAC TAC GCG CGC GCG
Gly Asp Ser Arg Glu Asn Phe Thr Ala Thr Leu Asp Trp Tyr Tyr Ala Arg Ala 837                                                    864
CCC CCG CGG TGC CTG CTG TAC TAC GTG TAC GAG CCC TGC ATC TAC CAC CCG CGC
Pro Pro Arg Cys Leu Leu Tyr Tyr Val Tyr Glu Pro Cys Ile Tyr His Pro Arg 891                                                    918
GCG CCC GAG TGC CTG CGC CCG GTG GAC CCG GCG TCC AGC TTC ACC TCG CCG GCG
Ala Pro Glu Cys Leu Arg Pro Val Asp Pro Ala Cys ser Phe Thr Ser Pro Ala 945                                                    972
CGC GCG GCG CTG GTG GCG CGC CGC GCG TAC GCC TCG TGC AGC CCG CTG CTC GGG
Arg Ala Ala Leu Val Ala Arg Arg Ala Tyr Ala Ser Cys Ser Pro Leu Leu Gly 999                                                   1026
GAC CGG TGG CTG ACC GCC TGC CCC TTC GAC GCC TTC GGC GAG GAG GTG CAC ACG
Asp Arg Trp Leu Thr Ala Cys Pro Phe Asp Ala Phe Gly Glu Glu Val His Thr 1053                                                   1080
AAC GCC ACC GCG GAC GAG TCG GGG CTG TAC GTG CTC GTG ATG ACC CAC AAC GGC
Asn Ala Thr Ala Asp Glu Ser Gly Leu Tyr Val Leu Val Met Thr His Asn Gly 1107                                                   1134
CAC GTC GCC ACC TGG GAC TAC ACG CTC GTC GCC ACC GCG GCC GAG TAC GTC ACG
His Val Ala Thr Trp Asp Tyr Thr Leu Val Ala Thr Ala Ala Glu Tyr Val Thr 1161                                                   1188
GTC ATC AAG GAG CTG ACG GCC CCG GCC CGG GCC CCG GGC ACC CCG TGG GGC CCC
Val Ile Lys Glu Leu Thr Ala Pro Ala Arg Ala Pro Gly Thr Pro Trp Gly Pro 1215                                                   1242
GGC GGC GGC GAC GAC GCG ATC TAC GTG GAC GGC GTC ACG ACG CCG GCG CCG CCC
Gly Gly Gly Asp Asp Ala Ile Tyr Val Asp Gly Val Thr Thr Pro Ala Pro Pro 1269                                                   1296
GCG CGC CCG TGG AAC CCG TAC GGC CGG ACG ACG CCC GGG CGG CTG TTT GTG CTG
Ala Arg Pro Trp Asn Pro Tyr Gly Arg Thr Thr Pro Gly Arg Leu Phe Val Leu 1323                                                   1350
GCG CTG GGC TCC TTC GTG ATG ACG TGC GTC GTC GGG GGG GCC GTC TGG CTC TGC
Ala Leu Gly Ser Phe Val Met Thr Cys Val Val Gly Gly Ala Val Trp Leu Cys 1377                                                   1404
GTG CTG TGC TCC CGC CGC CGG GCG GCC TCG CGG CCG TTC CGG GTG CCG ACG GGG
Val Leu Cys Ser Arg Arg Arg Ala Ala Ser Arg Pro Phe Arg Val Pro Thr Arg 1431                                                   1458
GCG GGG ACG CGC ATG CTC TCG CCG GTG TAC ACC AGC CTG CCC ACG CAC GAG GAC
Ala Gly Thr Arg Met Leu Ser Pro Val Tyr Thr Ser Leu Pro Thr His Glu Asp 1485                                                   1512
TAC TAC GAC GGC GAC GAC GAC GAC GAG GAG GCG GGC GAC GCC CGC CGG CGG CCC
Tyr Tyr Asp Gly Asp Asp Asp Asp Glu Glu Ala Gly Asp Ala Arg Arg Arg Pro 1539                                                   1566
TCC TCC CCC GGC GGG GAC AGC GGC TAC GAG GGG CCG TAC GTG AGC CTG GAC GCC
Ser Ser Pro Gly Gly Asp Ser Gly Tyr Glu Gly Pro Tyr Val Ser Leu Asp Ala 1593                                                   1620
GAG GAC GAG TTC AGC AGC GAC GAG GAC GAC GGG CTG TAC GTG CGC CCC GAG GAG
Glu Asp Glu Phe Ser Ser Asp Glu Asp Asp Gly Leu Tyr Val Arg Pro Glu Glu
```

```
                    1647                                              1674
GCG CCC CGC TCC GGC TTC GAC GTC TGG TTC CGC GAT CCG GAG AAA GCG GAA GTG
Ala Pro Arg Ser Gly Phe Asp Val Trp Phe Arg Asp Pro Glu Lys Pro Glu Val 1701                                              1728
ACG AAT GGG CCC AAC TAT GGC GTG ACC GCC AGC CGC CTG TTG AAT GCC CGC CCC
Thr Asn Gly Pro Asn Tyr Gly Val Thr Ala Ser Arg Leu Leu Asn Ala Arg Pro

1755
GCT TAA
Ala
```

CHART D

Bam HI 7 Fragment of PRV

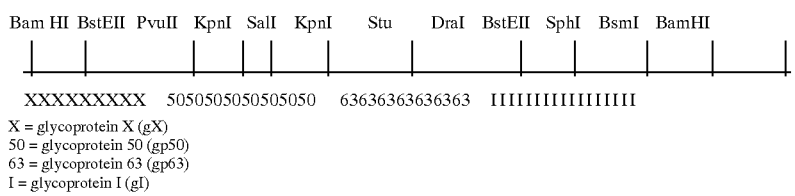

X = glycoprotein X (gX)
50 = glycoprotein 50 (gp50)
63 = glycoprotein 63 (gp63)
I = glycoprotein I (gI)

CHART E

Construction of pPR28-4 and pPR28-1

(a) Bam HI 7 is digested with BamHI and PvuII to yield fragments 1 (1.5 kb) and 2 (4.9 kb).

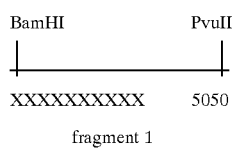

(b) Fragments 1 and 2 are serparately inserted between the BamHI and PvuII sites of pBR322 to produce

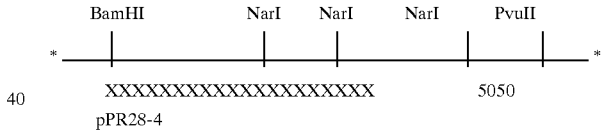

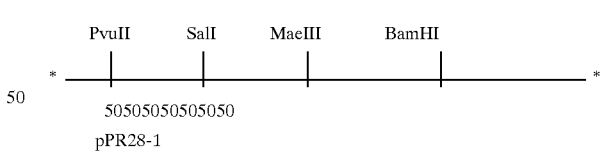

CHART F

Restriction Enzyme Cleavage Sites Used for pg50 Sequencing

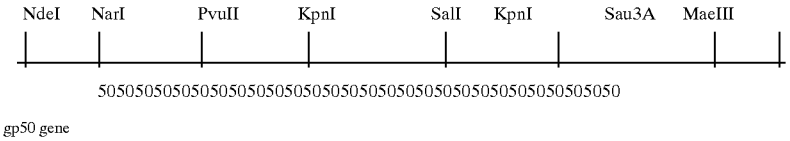

CHART G
Construction of pPR28-4 Nar2

(a) pPR28-4 is digested with NarI to produce fragment 3.

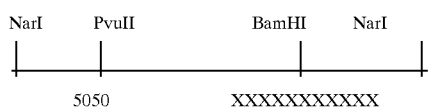

(b) BamHI linkers are added fragment and then it is treated with BamHI to produce fragment 4.

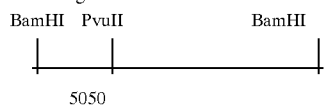

(c) Fragment 4 is circularized with DNA ligase to produce pPR28-4 Nar2.

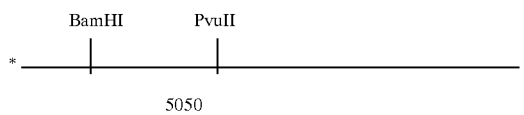

CHART H
Assembly of complete gp50 Gene (a) pPR28-4 Nar2 is digested with BamHI and PvuII to produce fragment 5 (160 bp).

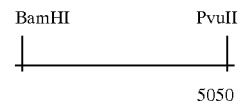

(b) pPR28-1 is digested with BamHI and PvuII to produce fragment 6 (4.9 kb).

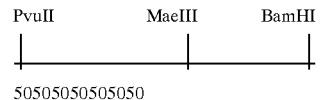

(c) pPGX1 is digested with BamHI, treated with BAP and then ligated with fragments 5 and 6 to produce pBGP50-23.

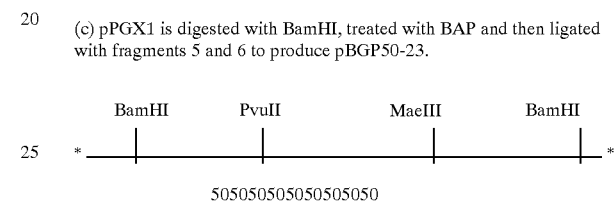

CHART I
Production of Plasmid pD50

(a) pBGP50-23 is cut with MaeIII, blunt-ended with T4 DNA polymerase and EcoRI linkers are added and digested with EcoRI, anf then cut with BamHI to produce fragment 7 (1.3 kb).

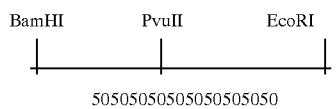

(b) Plasmid pSV2dhfr is cut with BamHI and EcoRI to obtain fragment 8 (5.0 kb).

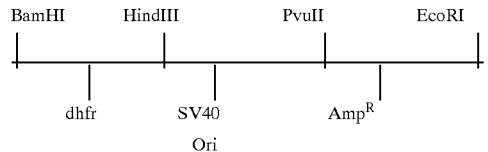

(c) Plasmid pD50 is produced by ligating fragments 7 and 8.

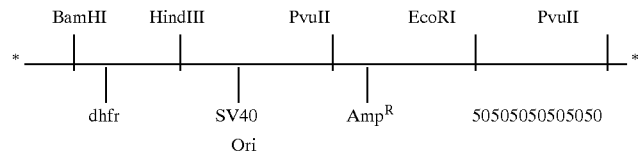

dhfr = Dihydrofolate reductase gene
SV40 Ori = SV40 promotor and origin of replication
$Amp^R$ = Ampicillin resistance gene

CHART J
Production of Plasmid pDIE50

(a) pD50 is digested with BamHI and treated with BAP to produce fragment 9.

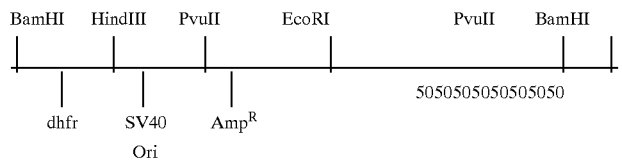

(b) Fragments 10 (760bp) containing the human cytomegalovirus (Towne) immediate early promoter is isolateed.

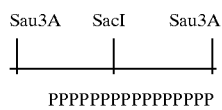

(c) Fragments 9 and 10 are ligated to produce plasmid pDIE50.

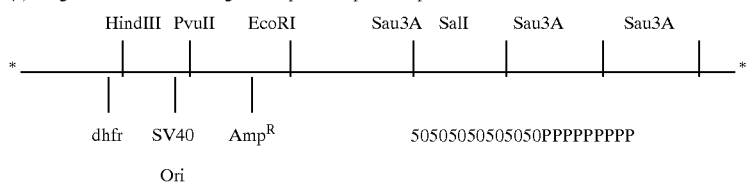

CHART K
Production of plasmid pDIE50PA (a) Plasmid pSVCOW7 is cut with PvuII and EcoRI to produce fragment 11.

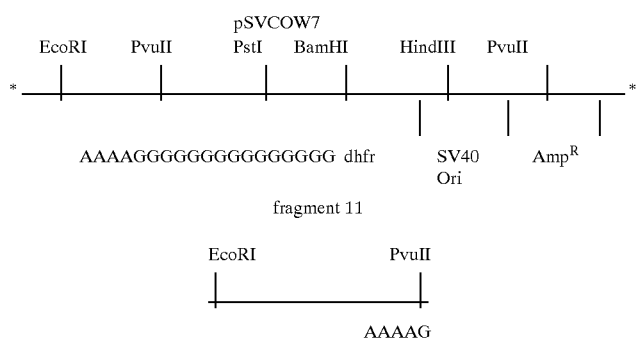

(b) Fragment 11 is cloned into pUC9 to produce plasmid pCOWT1.

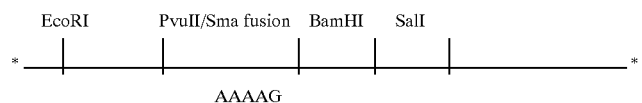

(c) pCOWT1 is cut with SalI, blunt-ended with T4 DNA polymerase, and EcoRI linkers are added followed by digestion wit EcoRI to produce fragment 12 (0.6 kb).

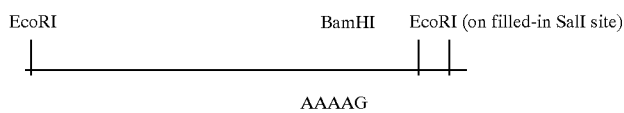

(d) Plasmid pDIE50 is cut with EcoRI and fragment 12 is cloned therein to produce plasmid pDIE50PA.

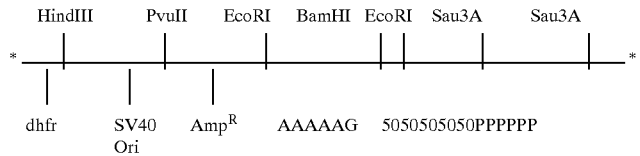

A = Bovine growth hormone polyadenylation signal
B = Genomic bovine growth hormone
P = Human cytomegalovirus (Towne) immediate early promoter

CHART L
Production of plasmid pDIE50T (a) Plasmid pDIE50 is digested with SalI and EcoRI to produce a 5.0 kb fragment,

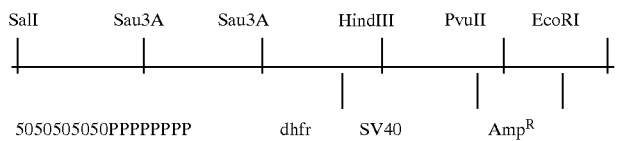

and a 0.7 kb fragment.

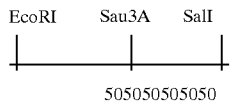

(b) The 0.7 kb fragment is digested with Sau3AI and a 0.5 kb SalI/Sau3AI fragment is isolated.

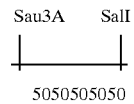

(c) The 5.0 kb EcoRI/SalI fragment, the 0.5 kb SalI/Sau3AI fragment and the annealed oligonucleotides (see text) are ligated to produce plasmid pDIE50T.

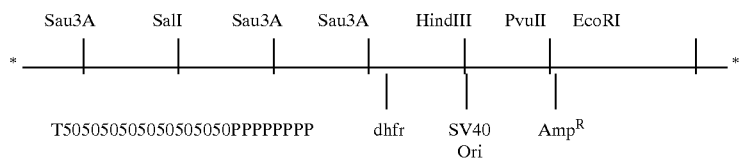

T = stop codon

CHART M
Restriction Enzyme cleavage Sites Used for pg63 Sequencing

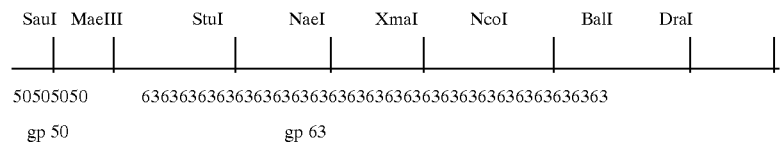

CHART N
Restriction Enzyme Cleavage Sites Used for gI Sequencing

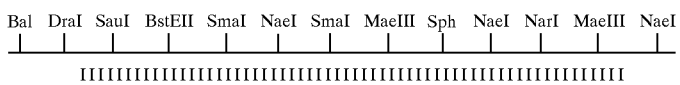

CHART O
Construction of Plasmid pUCD/B (a) A BamHI 7 fragment is cloned into plasmid pUC19 to produce plasmid A.

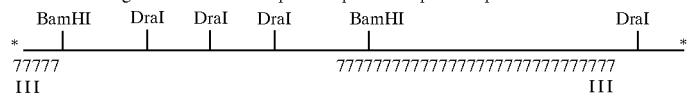

(b) Plasmid A is digested with DraI to produce fragment 1.

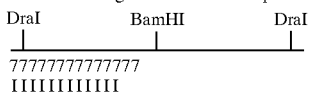

(c) BamHi linkers are added to fragment 1, followed by digestion with BamHI to produce fragment 2 (2.5 kb).

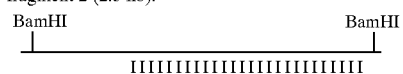

(d) Fragment 2 is cloned into pUC19 digested with BamHI to produce plasmid pUCD/B.

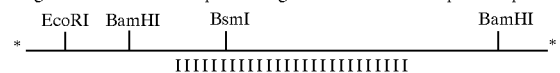

7 = BamHI 7 fragment
I = glycoprotein

CHART P
Construction of Plasmid pDGI (a) Plasmid pUCD/B is digested with BsmI and EcoRI to produce fragment 3 (4.4 kb).

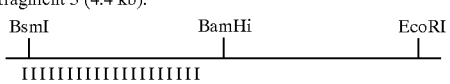

(b) The following two synthetic oligonucleotides are obtained:
   5′ CGCCCCGCTTAAATACCGGGAGAAG 3′
   5′ AATTCTTCTCCCGGTATTTAAGCGGGGCGGG 3′

(c) The synthetic oligonucleotides and fragment 3 are ligated to produce plasmid pGI.

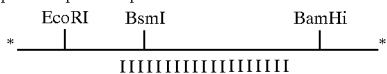

(d) Plasmid pGI is digested with EcoRI and BamHI to produce fragment 4 (1.8 kb).

(e) Plasmid pSV2dhfr is cut with EcoRI and then cut with BamHI to obtain fragment 5 (5.0 kb).

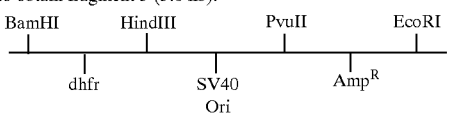

(f) Fragments 4 and 5 are then ligated to produce plasmid pDGI.

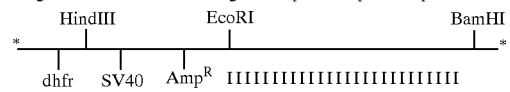

dhfr = Dihydrofolate reductase
SV40 Ori = SV40 promoter and origin of replication
$Amp^R$ = Ampicillin resistance

CHART Q
Construction of Plasmid pDIEGIPA (a) Plasmid pDGI is cut with BamHI to produce fragmant 6.

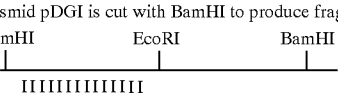

(b) Fragment 7 (760bp) containing the human cytomegalovirus (Towne) immediate early promoter is isolated.

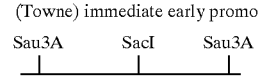

(c) Fragment 6 and 7 are ligated to produce plasmid pDIEGIdhfr.

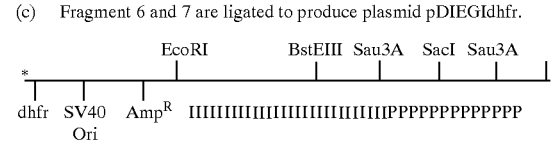

37
-continued (d) Plasmid pSVCOW7 is cut with PvuII and EcoRI to produce fragment 8.

```
                        pSVCOW7
    EcoRI    PvuII   PstI   BamHI  HindIII  PvuII
  *___|_____|_____|_____|_____|_____|___*
       AAAAGGGGGGGGGGGGGGGGGG dhfr  SV40    Amp^R
                                    Ori
                      Fragment 8
```

```
        EcoRI         PvuII
         |_____|
              AAAAG
```

(e) Fragment 8 is cloned in pUC9 to produce plasmid pCOWT1.
```
     EcoRI   PvuII/Sma fusion   BamHI      SalI
   *___|_____|_____|_____|___*
                        AAAAG
```

(f) pCOWT1 is cut with SalI, treated with T4 DNA polymerase, and EcoRI linkers are ligated on followed by digestion with EcoRI to produce fragment 9 (0.6 kb).

```
      EcoRI              BamHI     EcoRI (on filled-in SalI site)
       |_____|_____|
                 AAAAG
```

(g) Fragment 9 is cloned into the EcoRI site of pUC19 to produce plasmid pCOWT1E.
```
      EcoRI            BamHI       EcoRI
    *___|_____|_____|___*
                 AAAAG
```

(h) pCOWT1E is digested with EcoRI to produce fragment 10 (600 bp).
```
    EcoRI    BamHI                 EcoRI
     |_____|_____|
              GAAAA
```

(i) Plasmid pDIEGIdhfr is digested with EcoRI and ligated with fragment 10 containing the bGH polyadenylation signal to produce plasmid pDIEGIPA.
```
  EcoRI BamHI EcoRI BsmI    BstEII  Sau3A Sau3A
  *_|_____|____|_____|_____|_____|_____|___*
      AAAA    IIIIIIIIIIIIIIIIIIIIIIIPPPPPPPPPP   dhfr
```

A = Bovine growth hormone polyadenylation signal  
G = Genomic bovine growth hormone  
P = Human cytomegalorvirus (Towne) immediate early promoter

CHART R
Construction of pGP63dhfr (a) BamHi 7 is digested with BstEII, treated with T4 DNA polymerase and then cut with KpnI to yield fragment 1 (1.9 kb).
```
      KpnI      MaeIII       DraI        BstEII
       |_____|_____|_____|
              6363636363636363
```

(b) Fragment 1 is then cloned between the KpnI and SmaI sites of plasmid pUC19 to yield plasmid pPR28-1BK.
```
      KpnI      MaeIII       DraI        BstEII
    *__|_____|_____|_____|__*
              6363636363636363
```

(c) Plasmid pPR28-1BK is cut with DraI and MaeIII to yield fragment 2 (1.1 kb).
```
         MaeIII           DraI
           |_____|
              6363636363636363
```

38
-continued (d) Plasmid pSV2dhfr is cut with EcoRI, treated with T4 DNA polymerase, and then cut with BamHI to obtain fragment 3 (5.0 kb).

```
     BamHI        HindIII       PvuII      EcoRI, filled
       |_____|_____|_____|
            dhfr         SV40          Amp^R
                          Ori
```

(e) Two oligonucleotides are synthesized to produce fragment 4.

```
5´GATCCGCAGTACCGGCGTCGATGATGATGGTGGCGCGCGAC      3´
3´     GCGTCATGGCCGCAGCTACTACTACCACCGCGCGCTGCACTG 5´
```

(f) Fragments 2, 3, and 4 are then ligated to produce plasmid pGP63dhfr.

```
      HindIII         EcoRI           StuI        MaeIII BamHI
    *___|_____|_____|_____|_____|__*
          dhfr SV40  Amp^R   6363636363636363636363636363
                Ori
``` dhfr = Dihydrofolate reductase  
SV40 Ori = SV40 promoter and origin of replication  
Amp^R = Ampicillin resistance

CHART S (a) pGP63dhfr is digested with BamHI and treated with BAP to produce fragment 5.
```
      HindIII         EcoRI           StuI        MaeIII BamHI
       |_____|_____|_____|_____|
         dhfr SV40  Amp^R   6363636363636363636363636363
              Ori
```

(b) Fragment 6 (760bp) containing the human cytomegalovirus (Towne) immediate early promoter is isolated.
```
          Sau3A       SacI        Sau3A
            |_____|_____|
              PPPPPPPPPPPPPPPPP
```

(c) Fragments 5 and 6 are ligated to produce plasmid pIEGP63dhfr.
```
      HindIII       EcoRI          StuI       Sau3A  SacI  Sau3A
    *___|_____|_____|_____|_____|_____|__*
          dhfr SV40  Amp^R   6363636363636363636363PPPPPPPPPPPP
               Ori
```

What is claimed is:

1. A recombinant DNA molecule consisting of a purified and isolated polynucleotide sequence which is the DNA sequence as shown in Chart C, or a fragment thereof encoding a polypeptide displaying PRV antigenicity.

2. A host cell transformed with the recombinant DNA molecule of claim 1.

3. The host cell of claim 2, which is of bacterial, fungal, plant, or animal origin.

4. The host cell of claim 3, which is *E. coli*.

5. The host cell of claim 3, which is a yeast cell.

6. The host cell of claim 3, which is a Chinese hamster ovary (CHO) cell.

7. A recombinant DNA molecule consisting of a purified and isolated polynucleotide sequence encoding pseudorabies virus gI glycoprotein or a fragment thereof displaying PRV antigenicity, said DNA sequence being operatively linked to a heterologous expression control sequence and said gI glycoprotein having the amino acid sequence as shown in Chart C.

8. A host cell transformed with the recombinant DNA molecule of claim 7.

9. The host cell of claim 8 which is of bacterial, fungal, plant, or animal origin.

10. The host cell of claim 8 which is *E. coli.*

11. The host cell of claim 8 which is a yeast cell.

12. The host cell of claim 8 which is a Chinese hamster ovary (CHO) cell.

13. A recombinant DNA molecule comprising a purified and isolated DNA molecule having the DNA sequence as shown in Chart C or a fragment thereof encoding a polypeptide displaying PRV antigenicity, operatively linked to a heterologous expression control sequence.

14. A host cell transformed with the recombinant DNA molecule of claim 13.

15. The host cell of claim 14 which is of bacterial, fungal, plant or animal origin.

16. The host cell of claim 15 which is *E. coli.*

17. The host cell of claim 15 which is a yeast cell.

18. The host cell of claim 15 which is a Chinese hamster ovary (CHO) cell.

19. A method for producing a polypeptide displaying PRV gI antigenicity comprising the steps of culturing the host cell of claim 8 and collecting said polypeptide.

20. A method for producing a polypeptide displaying PRV gI antigenicity comprising the steps of culturing the host cell of claim 14 and collecting said polypeptide.

21. The method of claim 19 or 20, wherein the host cell is selected from the group consisting of bacteria, fungi, plant cells, and animal cells.

22. The method of claim 19 or 20, wherein the host cell is *E. coli.*

23. The method of claim 19 or 20, wherein the host cell is yeast.

24. The method of claim 19 or 20, wherein the host cell is CHO.

* * * * *